US008711149B2

(12) United States Patent
Schmidt et al.

(10) Patent No.: US 8,711,149 B2
(45) Date of Patent: Apr. 29, 2014

(54) GRAPHICAL USER INTERFACE FOR INTERPRETING THE RESULTS OF IMAGE ANALYSIS

(75) Inventors: Guenter Schmidt, Munich (DE); Arno Schaepe, Starnberg (DE); Gerd Binnig, Kottgeisering (DE)

(73) Assignee: Definiens AG, Munich (DE)

( * ) Notice: Subject to any disclaimer, the term of this patent is extended or adjusted under 35 U.S.C. 154(b) by 276 days.

(21) Appl. No.: 13/313,685

(22) Filed: Dec. 7, 2011

(65) Prior Publication Data

US 2012/0147010 A1 Jun. 14, 2012

Related U.S. Application Data

(60) Provisional application No. 61/459,180, filed on Dec. 8, 2010.

(51) Int. Cl.
*G06T 11/20* (2006.01)

(52) U.S. Cl.
USPC ............................ 345/440; 382/128; 715/771

(58) Field of Classification Search
CPC ............................ G06T 11/206; G06F 17/246
USPC ............................ 345/440; 715/771; 382/128
See application file for complete search history.

(56) References Cited

U.S. PATENT DOCUMENTS

| | | | | |
|---|---|---|---|---|
| 2002/0175949 A1* | 11/2002 | Kaushikkar et al. | .......... | 345/781 |
| 2005/0114801 A1* | 5/2005 | Yang et al. | ............... | 715/961 |
| 2006/0093207 A1* | 5/2006 | Reicher et al. | ............... | 382/156 |
| 2008/0130964 A1* | 6/2008 | Zwirn et al. | .................. | 382/128 |
| 2010/0064374 A1* | 3/2010 | Martin et al. | ................... | 726/27 |
| 2010/0075373 A1* | 3/2010 | Hoyt | ........................... | 435/40.5 |

* cited by examiner

*Primary Examiner* — Maurice L McDowell, Jr.
(74) *Attorney, Agent, or Firm* — Imperium Patent Works; Darien K. Wallace

(57) ABSTRACT

A method of intuitively displaying values obtained from analyzing bio-medical images includes displaying a table of the values in a first pane of a graphical user interface. The table contains a user selectable row that includes a reference value and two numerical values. The reference value refers to an image of a tissue slice. The first numerical value is generated by performing image analysis on the image, and the second numerical value indicates a health state of the tissue. The image is displayed in a second pane of the graphical user interface in response to the user selecting the user selectable row. A graphical plot with a selectable symbol associated with the image is displayed in a third pane. The symbol has a position in the plot defined by the values. Alternatively, in response to the user selecting the selectable symbol, the image is displayed in the second pane.

39 Claims, 17 Drawing Sheets

FIG. 15

GRAPHICAL USER INTERFACE FOR INTERPRETING THE RESULTS OF IMAGE ANALYSIS

CROSS REFERENCE TO RELATED APPLICATION

This application claims the benefit under 35 U.S.C. §119 of provisional application Ser. No. 61/459,180, entitled "Content Driven Image Mining to Generate Image-Based Biomarkers", filed on Dec. 8, 2010, the subject matter of which is incorporated herein by reference.

TECHNICAL FIELD

The present invention relates generally to image analysis, and more specifically to a system for computer-aided diagnosis and prognosis that displays the results of the analysis of bio-medical images on a versatile and intuitive user interface.

BACKGROUND

Systems for detecting and analyzing target patterns in digital imagery have a wide variety of uses. An increasingly important area is the detection and analysis of anatomical regions in the human body. For example, radiological images from computed tomography (CT) are used for the computer-aided detection (CAD) of various ailments in human organs. Images from magnetic resonance imaging (MRI) are also used in computer-aided detection. The large amount of information generated by computer-aided detection systems is difficult for pathologists and radiologists to assimilate. Pathologists and radiologists currently base their diagnoses only on a small portion of the overall information that they choose based on subjective criteria.

An improved graphical user interface is sought that displays the large amount of information generated by image analysis of bio-medical images in an easily accessible, intuitive and cross-referenced manner.

SUMMARY

A method of displaying tables, graphs and plots of the results of image analysis on bio-medical images includes displaying a table of values in a first pane of a graphical user interface. The table contains a user selectable row that includes a reference value, a first numerical value and a second numerical value. The reference value refers to a digital image of a tissue slice of the patient from whom the tissue depicted in the digital image was taken. The first numerical value is generated by performing image analysis on the image, and the second numerical value indicates a health state of the tissue. The image is displayed in a second pane of the graphical user interface in response to the user selecting the user selectable row. A graphical plot with a selectable symbol associated with the image is displayed in a third pane. The symbol has a position in the plot defined by the values. Alternatively, in response to the user selecting the selectable symbol, the image is displayed in the second pane A computer program product tangibly embodied on a computer-readable storage medium provides a visual display of a graphical user interface showing the results of image analysis. The graphical user interface includes a first pane and a second pane. The first pane displays a graphical plot including a user selectable symbol associated with a digital image of a slice of tissue. The user selectable symbol has a position in the graphical plot defined by first and second numerical values generated by image analysis of the digital image. The user selectable symbol represents the health state of the patient from whom the tissue was taken. The health state is defined by a third numerical value that is determined by image analysis of the digital image, by manual review of the digital image by a pathologist or by using context information for the patient, such as molecular diagnostics information. The second pane displays the digital image in response to the user selecting the selectable symbol.

Another method of displaying the results of image analysis includes displaying a first image analysis value in a table in a first pane of a graphical user interface. The first image analysis value is generated by analyzing a digital image of a slice of tissue using a first parameter. A list of selectable statistical methods is displayed in a second pane of the graphical user interface. A second parameter is computed using a statistical method after the user has selected that statistical method from the list. A second image analysis value is displayed in the table after the user has selected the statistical method. The second image analysis value is generated by analyzing the digital image using the second parameter. A new version of the digital image is displayed in a third pane of the graphical user interface after the user has selected the statistical method. The new version of the digital image is generated by analyzing the digital image using the second parameter.

In another embodiment, an image-based biomarker is generated using image features obtained through object-oriented image analysis of medical images. The values of a first subset of image features are measured and weighted. The weighted values of the image features are summed to calculate the magnitude of a first image-based biomarker. The magnitude of the biomarker for each patient is correlated with a clinical endpoint, such as a survival time, that was observed for the patient whose medical images were analyzed. The correlation is displayed on a graphical user interface as a scatter plot. A second subset of image features is selected that belong to a second image-based biomarker such that the magnitudes of the second image-based biomarker for the patients better correlate with the clinical endpoints observed for those patients. The second biomarker can then be used to predict the clinical endpoint of other patients whose clinical endpoints have not yet been observed The image analysis program generates image-based biomarkers that predict clinical endpoints of patients. Data mining techniques are combined with image analysis to achieve context-driven image mining. An image-based biomarker is a predetermined set of image features weighted and combined in a predetermined manner to provide an indication of a clinical endpoint, such as a survival time or a disease recurrence probability.

In one method, an image-based biomarker is generated that better correlates with the clinical endpoint. The image-based biomarker is generated using image features obtained through object-oriented image analysis of medical images. The values of a first subset of image features are measured. Each of the values is then weighted. The magnitude of the first image-based biomarker is calculated by summing the weighted values of all of the image features. The magnitude of the biomarker for each patient is correlated with a clinical endpoint that was observed for the patient whose medical images were analyzed. How the first image-based biomarker correlates with the clinical endpoint observed for each of the patients is displayed on a graphical user interface as a scatter plot.

A second subset of image features is then selected that belong to a second image-based biomarker such that the magnitudes of the second image-based biomarker better correlate with the clinical endpoints observed for the patients. The second biomarker can then be used to predict the clinical endpoint of other patients whose clinical endpoints have not yet been observed.

In another method, an additional image-based biomarker is generated that better correlates with a subgroup of outlier points representing patients whose clinical endpoints do not correlate well with the baseline image-based biomarker. Pixel values of medical images of a group of patients are first acquired. Objects of a data network for each of the medical images are generated by linking selected pixel values to selected objects according to a class network and a process hierarchy. The objects are measured to obtain a value for each of a plurality of image features. A first subset of the image features is selected that belong to a first image-based biomarker. The first image-based biomarker is correlated for each of the patients with a clinical endpoint observed for that patient. How the first image-based biomarker correlates with the clinical endpoint observed for each of the patients is displayed on a graphical user interface, for example in a scatter plot. A subgroup of the patients is identified for which the first image-based biomarker correlates poorly with the clinical endpoints observed for the patients in the subgroup. For example, the subgroup includes the points of the scatter plot that are farthest away from a linear regression line through the middle of the largest group of points.

A second subset of the image features is then selected that belongs to a second image-based biomarker that better correlates with the clinical endpoints observed for the patients in the subgroup. The second image-based biomarker can then be used to predict the clinical endpoint of patients whose clinical endpoints have not yet been observed and for whom the first image-based biomarker results in a magnitude that falls outside a predefined base range.

Other embodiments and advantages are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

FIG. 15 is a screenshot with a list of the values of image features that make up the image-based biomarker.

DESCRIPTION

Figure 1:
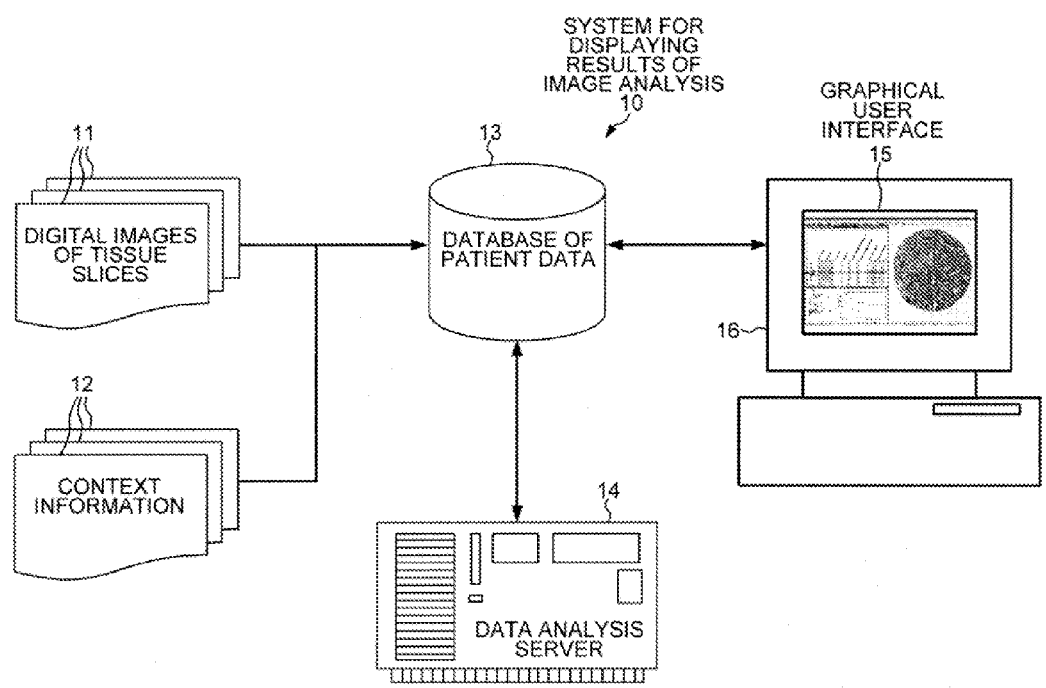
FIG. 1 is a diagram of a system for displaying the results of image analysis of bio-medical images on a graphical user interface.

FIG. 1 shows a system 10 for displaying tables, graphs and plots of the results of image analysis on bio-medical images. The bio-medical images 11 can be acquired using various imaging devices, such as a computed tomography (CT) device, a magnetic resonance imaging (MRI) device, a positron emission tomography (PET) device or a regular light microscope. For example, the images are obtained from tissue slices used in pathology, from CT scans used in radiology, or from laboratory work on blood samples. Input data for the image analysis can also include patient medical history and demographic data that is used as context information 12 for calculating parameters used in the image analysis. For example, the size of organs depends on the age of the person, and the range for those sizes can be calculated by using the age of the patient as context information.

The acquired digital images 11 as well as the context information 12 are stored in a database 13 of patient data. Image analysis software executing on a data analysis server 14 then performs intelligent image processing and automated classification and quantification. The image analysis software is a computer program product tangibly embodied on a computer-readable storage medium in server 14 and comprises computer readable and executable program instructions that when executed by a processor on server 14 provide a visual display of the user's graphical user interface 15 on an interconnected display device 16, such as a personal computer. The image analysis software transforms weakly structured input data in the form of pixels into a hierarchical network of objects. This transformation occurs via a large number of intermediate steps, in which intermediate objects, which in the end are not relevant, are generated. These intermediate objects gradually develop into the ultimate relevant objects.

The image analysis program prepares links between some objects and thereby generates higher hierarchically ranked objects. The image analysis program provides the higher hierarchically ranked objects with properties, classifies them, and then links those objects again at a still higher level to other objects. The higher hierarchically ranked objects are used to find target objects in the images more rapidly. More easily detected starting objects are first found and then used to identify hard-to-find objects in the hierarchical data structure. Detecting hard-to-find target objects is faster using links in the hierarchical data network than using process-based procedures such as indexing.

Both general and subject-specific knowledge is used to classify and segment objects in the images. The knowledge and the program flow of the image analysis program are separated in the software structure. The parameters by which the image analysis is performed, for example thresholds of size or brightness, can be changed without having to revise the process hierarchy of software steps. The image analysis software allows the process hierarchy (program flow) as well as the results of the image analysis to be visualized on the graphical user interface 15. The program flow is displayed as a process hierarchy in one pane of the graphical user interface 15. The image analysis software displays segmented images in another pane. Classified and segmented objects in the digital images are marked or highlighted to correspond to their classification. Values corresponding to the properties of the segmented objects and of each segmented image as a whole are displayed in lists, tables, graphs and plots in other panes of the graphical user interface 15. For example, the contour of a segmented and classified object is given an identifying color. Objects that have a membership in the same class are depicted in the same color.

Figure 2:
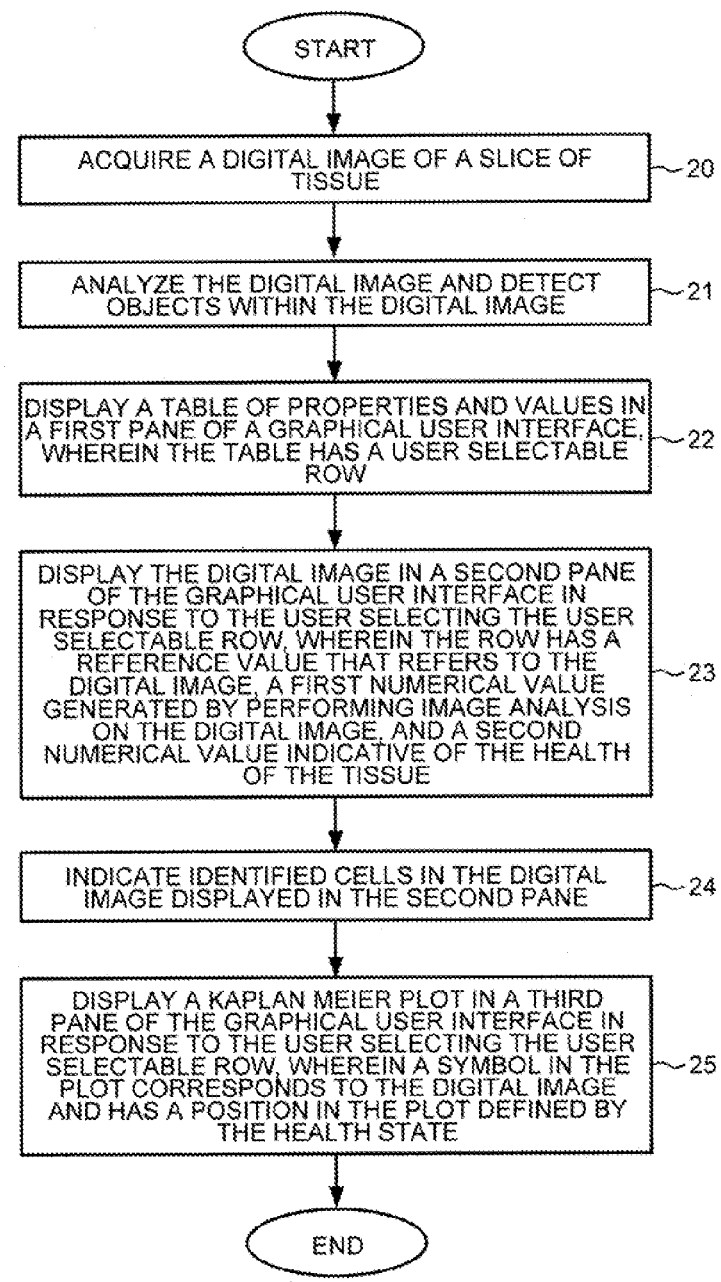
FIG. 2 is a flowchart of a method for displaying the results of the analysis of bio-medical images on a versatile and intuitive user interface.
Figure 3:
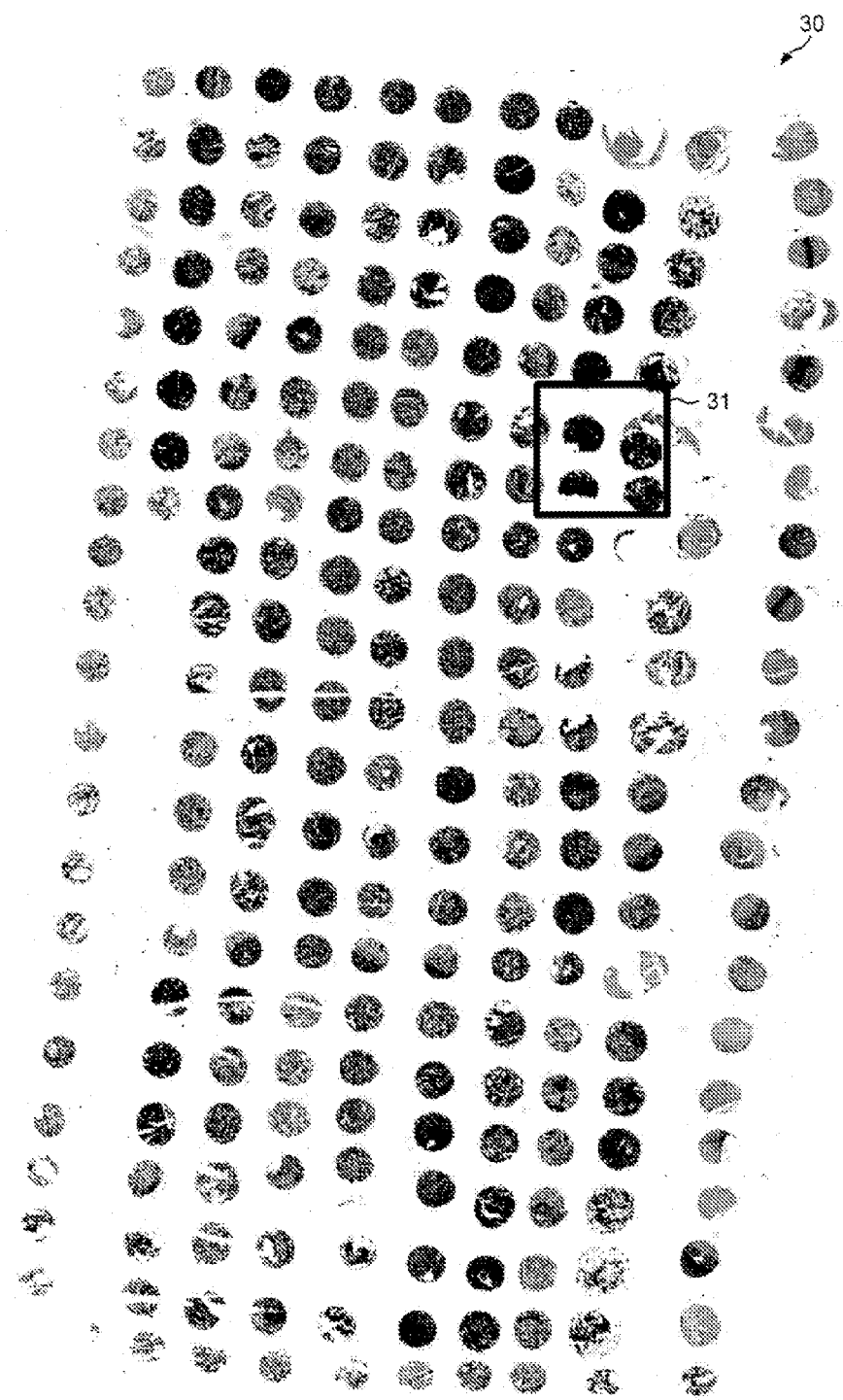
FIG. 3 shows a tissue micro array from which the images for the method of FIG. 2 are acquired.

FIG. 2 is a flowchart of a method by which system 10 displays the results of the analysis of bio-medical images on a versatile and intuitive user interface. The method displays tables and those images associated with the rows of the table on graphical user interface 15. In a first step 20, system 10 acquires the digital images 11. FIG. 3 shows an example of digital images 11 that are input into database 13 of system 10. FIG. 3 shows a tissue micro array 30 made up of slices of biopsy tissue cores taken from a plurality of esophagogastric cancer patients. The digital images input into system 10 can be images of tissue slices stained with various biomarkers, such as hematoxylin and eosin (HE), Human Epidermal growth factor Receptor 2 (Her2), Her2/neu cytoplasmic stain, estrogen receptor (ER) stain, progesterone receptor (PR) stain, tumor marker Ki67, Mib, SishChr17, SishHer2, cluster of differentiation 44 (CD44) antibody stain or CD23 antibody stain. In many cases, the digital images operated upon by system 10 depict only a portion of the slices of tissue.

In step 21, data analysis server 14 of system 10 analyzes the digital images 11 using object-oriented pattern recognition and detects objects in the digital images 11. For each image, a data network is generated by linking selected pixel values to selected objects according to a class network and a process hierarchy. The digital images are classified and segmented into objects that fall within object classes such as: tubulus, gland, vessel, epithelium, stroma, cell, nucleus, cytoplasm, membrane, micronucleus, chromatin and reticulum. For example, objects are generated for all of the cells and cell parts in the images of the tissue micro array 30 in order to identify cancerous regions of interest.

Then properties and values are generated using statistical values from different kinds of object groups. The image analysis software performs object-oriented analysis and generates a table listing the properties and values associated with the objects contained in the digital images. Each object group is defined by the classification of the objects in combination with additional conditions. For example, the average size of all nuclei is calculated, as well as the average size of all cancer nuclei or of all cancer nuclei fulfilling a particular condition, e.g., with respect to their color or shape. The table of properties and values is numerically based and can thus be generated with a high degree of automation. Creating a complex table listing properties with the corresponding values manually would be prohibitively expensive. Physicians currently evaluate microscopic images manually using qualitative or semi-quantitative scoring methods. But there is currently no numerical basis for objective judging the tissue state based on an image.

Figure 4:
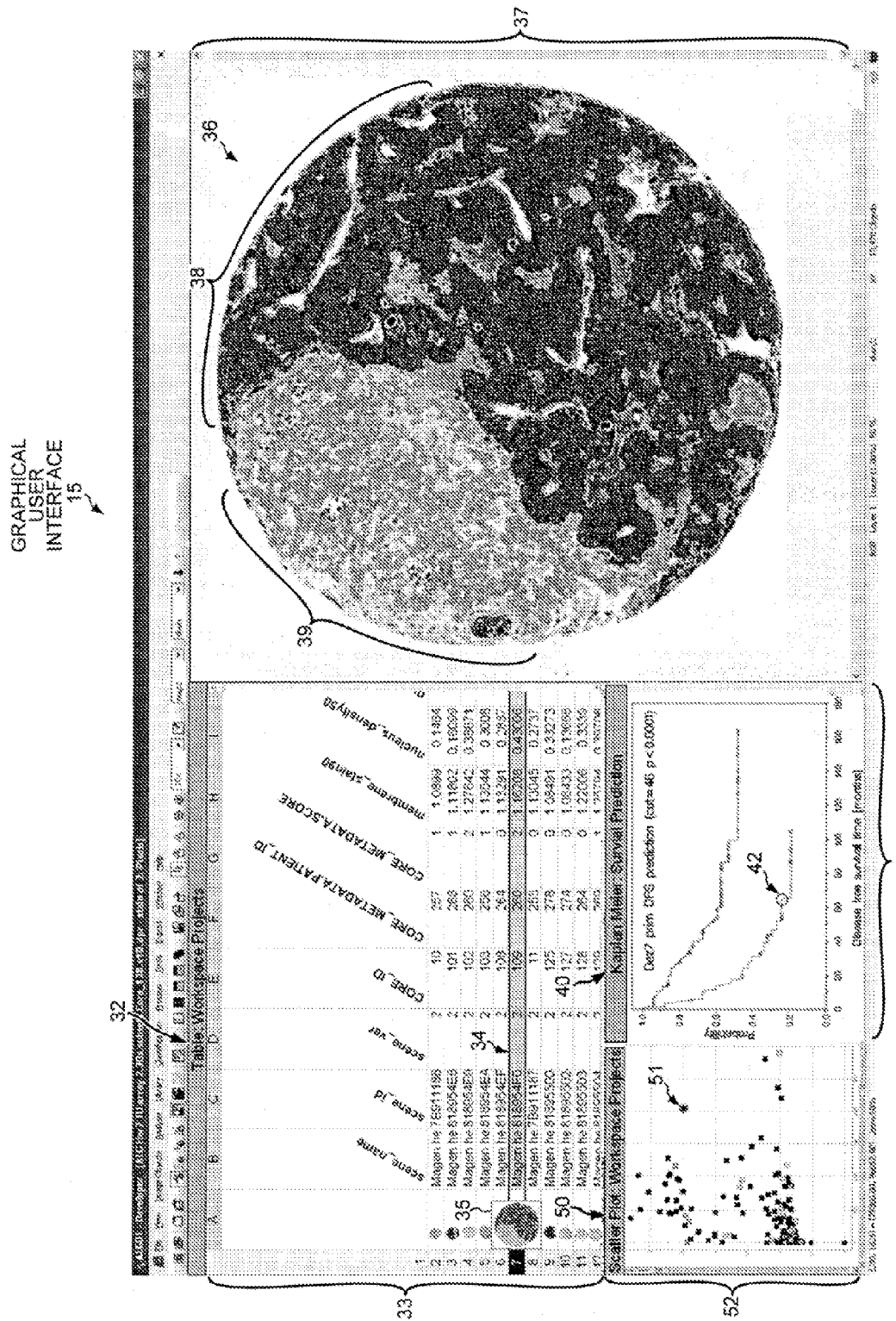
FIG. 4 is a screenshot of a graphical user interface that includes a scatter plot, a table of image analysis values, a Kaplan-Meier graph, and an image of a slice of tissue from the tissue micro array of FIG. 3.

In step 22, the table 32 of properties and values is displayed in a first pane 33 of the graphical user interface 15, as shown in FIG. 4. Table 32 includes a user selectable row 34 that includes a reference value, a first numerical value and a second numerical value. The reference value refers to a digital image of a slice of tissue. In the example of FIG. 4, the highlighted row 34 has been selected and corresponds to the digital image shown in a thumbnail image 35 at the left of the row.

In step 23, a higher resolution version 36 of the digital image 35 corresponding to user selectable row 34 is displayed in a second pane 37 of the graphical user interface 15 in response to the user selecting the user selectable row 34. The user selects user selectable row 34 by clicking on any location in the row. Digital image 36 depicts one of the biopsy tissue cores shown in FIG. 3. The image analysis program has recognized, segmented, and classified objects in digital image 36.

Figure 13:
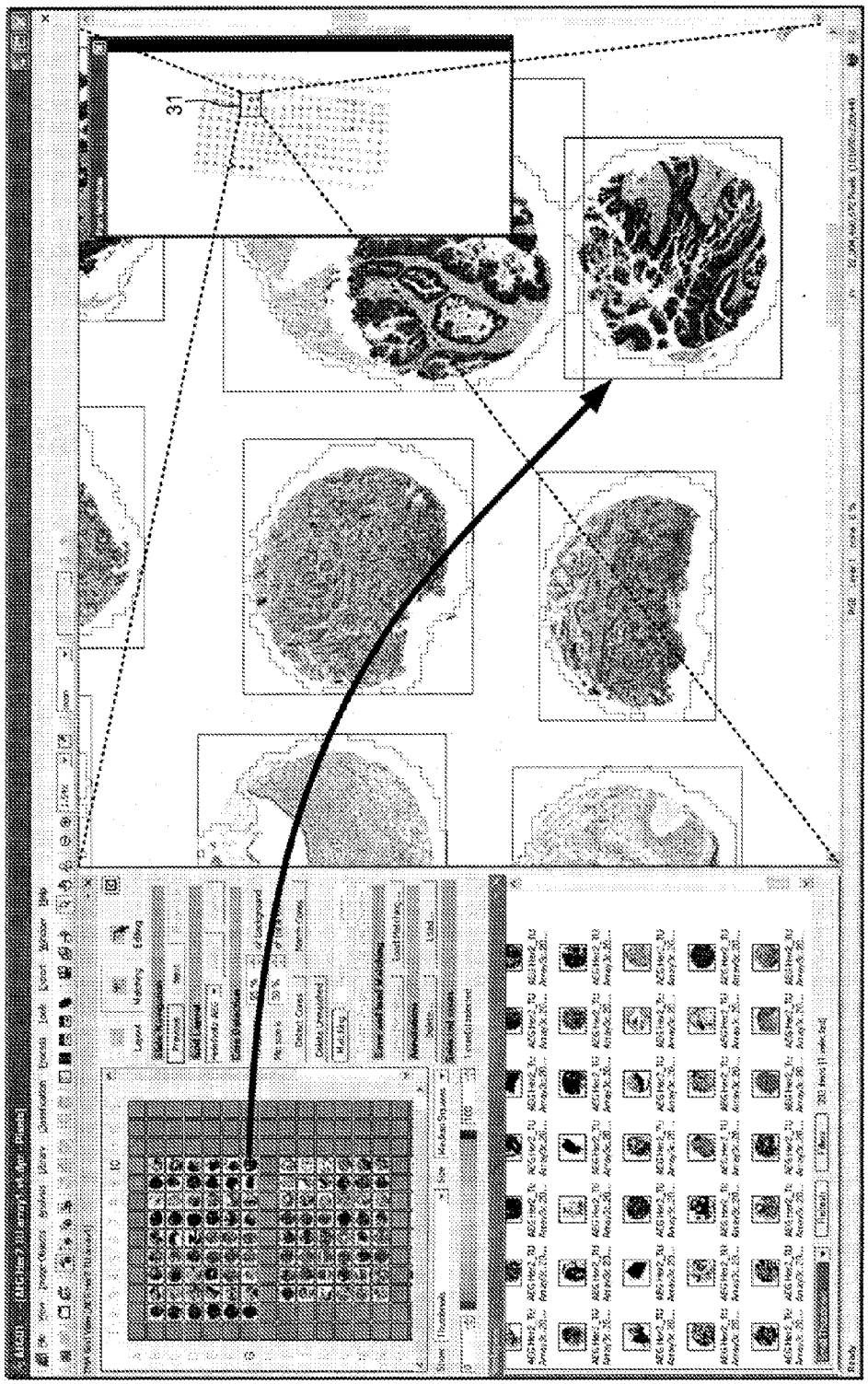
FIG. 13 is a screenshot of the graphical user interface of the image analysis program showing a portion of the tissue micro array of FIG. 3.

Multiple digital images can be displayed together in second pane 37 in response to the user selecting multiple selectable rows. The lower left pane in FIG. 13 shows multiple digital images of tissue slices displayed together in an image gallery manner. A distinct reference value in each user selectable row refers to a different digital image in the pane of the graphical user interface. The pane to the right in FIG. 13 shows higher resolution versions of digital images of tissue slices also displayed together in an image gallery manner. Objects that are identified in the digital images are outlined in the higher resolution versions of the digital images.

In step 24, identified cells are indicated in the image displayed in second pane 37. Examples of identified cells are mitotic cells, tumor cells, cells exhibiting an overexpression of a protein, cells exhibiting an overamplification of a gene, and inflamed cells. The displayed image 36 shows the classification of the segmented objects in the digital image by assigning a specific color to the border of the objects that belong to a class or by filling the objects with the color or texture of the class. For example, the image analysis program has identified and highlighted cancer cells 38 towards the right of image 36 and normal cells 39 towards the left of image 36.

In the example of FIG. 4, the reference value of user selectable row 34 that refers to image 36 is "818954F0" and is listed in the column labeled "scene_id". The first numerical value of user selectable row 34 is the value in the column labeled "membrane_stain90". The first numerical value for row 34 is 1.16208 and represents the intensity of staining by the biomarker of the tumor cell membranes identified in image 36. The value represents the staining intensity of the 90th percentile of stained cells. So 90% of the cells have membranes that are stained to an intensity of 1.16208 or less. The second numerical value of user selectable row 34 is the value in the column labeled "CORE_METADATA.SCORE". The second numerical value for row 34 is "2" and indicates the health state of the tissue depicted in digital image 36. The second numerical value can be assigned by the image analysis program based on the objects recognized in image 36, or a pathologist can assign a health state value to each image after inspecting the images. Where the health state of the tissue is determined by the image analysis program, the determination can be made based on the expression status of a protein such as the estrogen receptor protein (ER), the progesterone receptor protein (PR), the KI67 protein, or the HER2neu protein. The image analysis program determines the expression status mainly by analyzing the intensity of the staining from the respective protein in segmented objects. The objects whose staining is determined are segmented based on applying a statistical method to the first numerical value. In the example of FIG. 4, objects are generated by applying a decision tree, a linear regression plot, a support vector machine, or a Bayes classifier to the membrane staining intensity indicated by the first numerical value. In one example, the health state of the tissue indicates the disease free survival time or the overall survival time of the patient from whom the biopsy tissue core depicted in image 36 was taken.

The first numerical value of user selectable row 34 is generated by performing image analysis on digital image 36. Other image analysis values besides the basic staining intensity of cell membranes can be displayed as the first numerical value. Examples of other image analysis values are the Allred score, the Gleason score, the Elston-Ellis score, and the HercepTest score.

The Allred score ranges from 0-8 and indicates the percentage of cells that have been stained to a certain intensity by the estrogen receptor (ER) antibody. Thus, the Allred score is the composite of a proportion score and an intensity score. The Allred score is indicative of breast cancer. An Allred score of three or more indicates ER positivity and can correspond to as few as 1% of the cells showing a weak immunostaining signal. The image analysis program calculates the Allred score by segmenting cell objects and then determining the average intensity of the staining color in the pixels within the cell objects.

The Gleason score ranges from 1-5 and is indicative of prostate cancer. The Gleason score is based on the architectural pattern of the glands of the prostate tumor. Cancer cells that are not able to structure themselves into glands resembling those of the normal prostate are assigned a score of five signifying aggressively malignant, whereas cancer cells that have a normal gland architecture are assigned a score of one signifying not very malignant. By generating hierarchically ranked objects in a hierarchical data network, the image analysis program is able to classify gland objects made up of cancer cells as having a normal gland architecture or various degrees of undifferentiated architectures.

The Elston-Ellis score is a grade ranging from I-III indicative of the severity of breast cancer. A grade of III indicates the most aggressive cancer, whereas the tumor cells of grade I breast cancer are not dividing rapidly. The grade is determined by summing the points assigned to three parameters: tubule formation, nuclear pleomorphism and mitosis per ten high-power fields (HPF) of 400×. Each of the parameters can have a point score ranging from 1-3 (1 being the best, and 3 being the worst). Thus, a sum of three results in a grade of I, whereas a sum of nine results in a grade of III. The image analysis program is able to determine the proportion of tubules, the similarity of nucleus sizes and the number of dividing cells per high power field of 400× magnification.

The HercepTest™ score ranges from 0 through 3+ and is indicative of the severity of breast cancer. A score of 3+ is positive for the type of breast cancer that can be treated with Herceptin™ (trastuzumab), whereas scores of 0 and 1+ are negative. The HercepTest represents the level of HER2 protein overexpresssion based on the degree of membrane staining. Complete membrane staining of some tumor cells results in a score of 3+ irrespective of the percentage of tumor cells that are stained. The image analysis program is able to determine whether each membrane object has the stain color around the entire membrane. Thus, the image analysis program searches for "O" shaped HER2 staining as opposed to "U" shaped or "‖" shaped staining.

In step 25, a Kaplan-Meier plot 40 is displayed in a third pane 41 of the graphical user interface 15. In response to the user selecting the user selectable row 34, a symbol 42 is displayed in the Kaplan Maier plot 40. The symbol 42 has a position in the Kaplan Meier plot defined by the health state as indicated by the second numerical value. Thus, the symbol 42 (a circle) indicates that the predicted disease free survival (DFS) time is about 65 months for the patient from whom the biopsy tissue core depicted in image 36 was taken. System 10 predicts the survival time by placing the patient in that group of prior patients with clinically observed survival times whose biopsy tissues exhibited similar image analysis characteristics as those of image 36.

Figure 5:
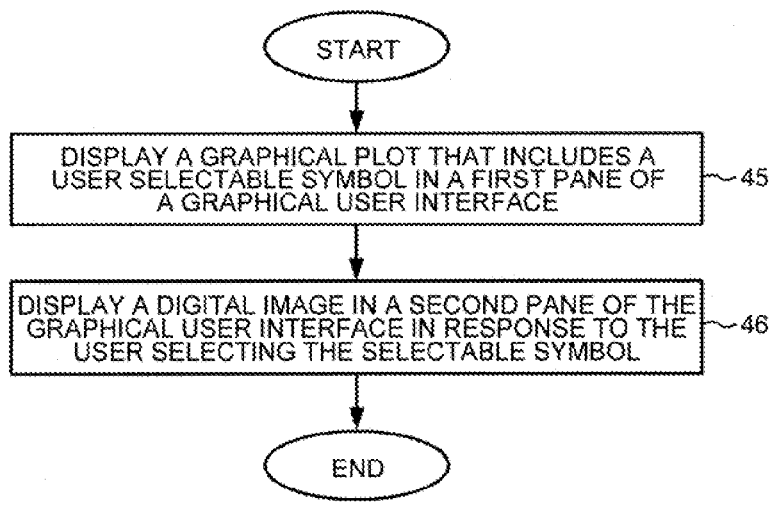
FIG. 5 is a flowchart of another method for displaying the results of the analysis of bio-medical images in a graphical plot on a user interface.

FIG. 5 is a flowchart of another method by which system 10 displays the results of the analysis of bio-medical images in a graphical plot on a user interface. In a step 45, a graphical plot 50 that includes a user selectable symbol 51 is displayed in a fourth pane 52. In FIG. 5, the symbol 51 is a circle around a square. The user selectable symbol 51 is associated with the digital image 36 of the slice of the biopsy tissue core. The user selectable symbol 51 has a position in the graphical plot 50 defined by the first numerical value and the second numerical value in row 34. For example, the position of symbol 51 along the y and x axes of the graphical plot 50 corresponds to the membrane staining intensity as represented by the first numerical value "membrane_stain90" and the nuclear staining intensity as represented by the second numerical value "nucleus_density50", respectively. The first and second numerical values are generated by image analysis of the digital image 36. The symbol 51 represents the health state of the tissue depicted in digital image 36. For example, different symbols corresponding to different images are depicted in colors that indicate the health state of the tissue in the respective images.

In the example of FIG. 4, a third numerical value in the column labeled "CORE_METADATA.SCORE" indicates the health state of the tissue in the image associated with each row. The third numerical value can have a value of 0, 1, 2 or 3. Thus, the symbols associated with images having the health states 0, 1, 2 and 3 are depicted in different colors, such as red, black, blue and yellow. The third numerical value in row 34 associated with image 36 is "2", and therefore the symbol 51 is depicted in blue. The third numerical value can be generated by the image analysis program based on the objects recognized in image 36. Alternatively, a pathologist can assign a health state value to each image after inspecting the images. In one example, the health state value indicates a range of the predicted disease free survival time of the patient from whom the biopsy tissue core depicted in image 36 was taken.

In another example, the third numerical value is indicative of the health state of just a portion of the tissue depicted in image 36. The third numerical value can indicate the health state of normal tissue, in-situ cancer tissue, and distant metastasis tissue. For example, in-situ cancer tissue could be breast cancer cells that have remained in the breast, whereas distant metastasis tissue could be breast cancer cells that have migrated to the liver. The third numerical value would indicate the state of only the cancer cells in the breast or in the liver.

In step 46, the digital image 36 of the slice of the biopsy tissue core is displayed in the second pane 37 in response to the user selecting the selectable symbol 51. In another embodiment, the first numerical value indicates an intensity of immunohistochemical staining of cancer cells in the digital image 36 of the slice of tissue, and the second numerical value indicates a proportion of stained cells in a portion of the digital image 36.

Figure 6:
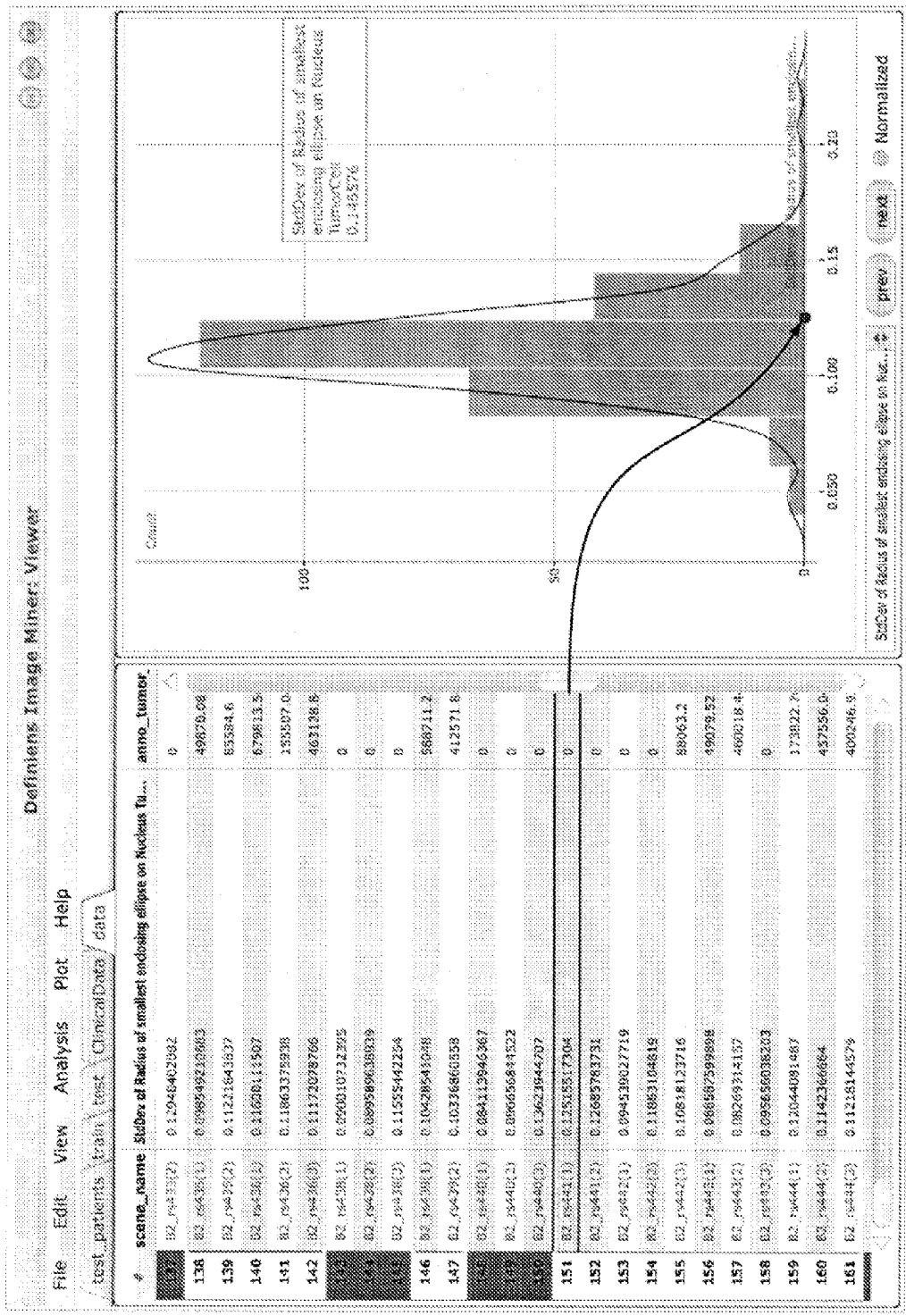
FIG. 6 is a screenshot of a graphical user interface that displays a histogram plot in a pane at the right.

Other examples of graphical plots that can be displayed in fourth pane 52 in step 45 of the method of FIG. 5 include scatter plots, line plots, and histogram plots. FIG. 6 shows a histogram plot displayed in the right pane of a graphical user interface. The histogram plot represents the distribution of a numerical value obtained through image analysis of multiple digital images. The numerical value plotted in the histogram plot of FIG. 6 is the standard deviation of the radius of the smallest ellipse that encloses the nucleus of each tumor cell. The table in the left pane in FIG. 6 indicates that the standard deviation numerical value is 0.125155 for the image of the tissue from patient #151. Because the row for patient #151 has been selected, the row is framed and the value of the standard deviation numerical value is indicated by a symbol on the histogram plot. The histogram plot shows how the standard deviation numerical values are distributed among all of the images of the tissue slices for the patients.

Figure 7:
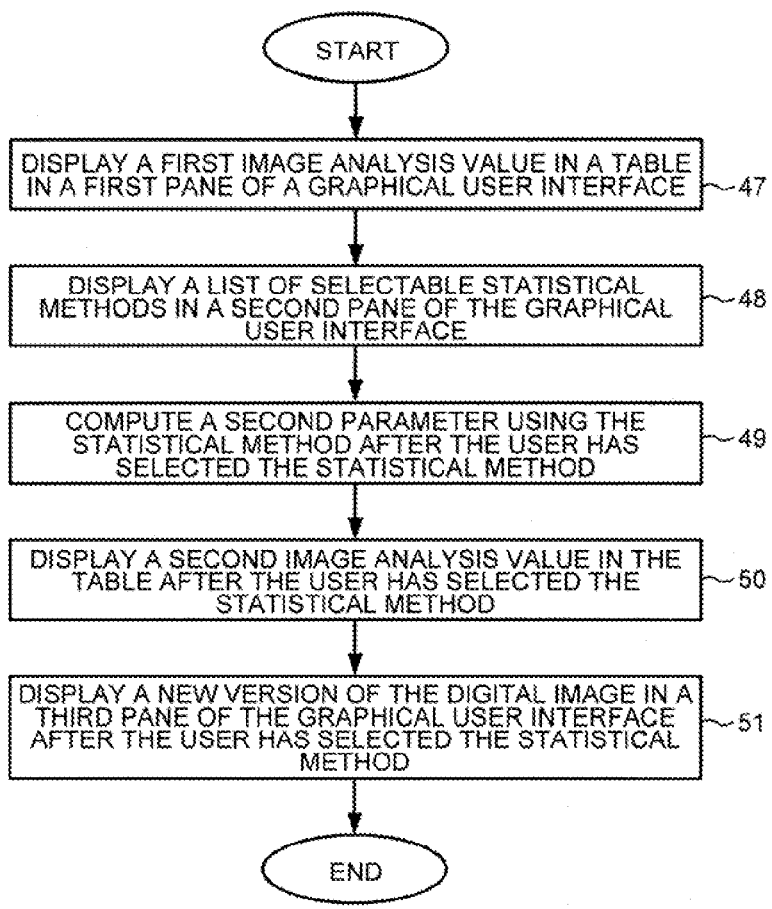
FIG. 7 is a flowchart of yet another method for displaying the results of the analysis of bio-medical images by displaying image analysis values and a new version of the image being analyzed.
Figures 8, 9:
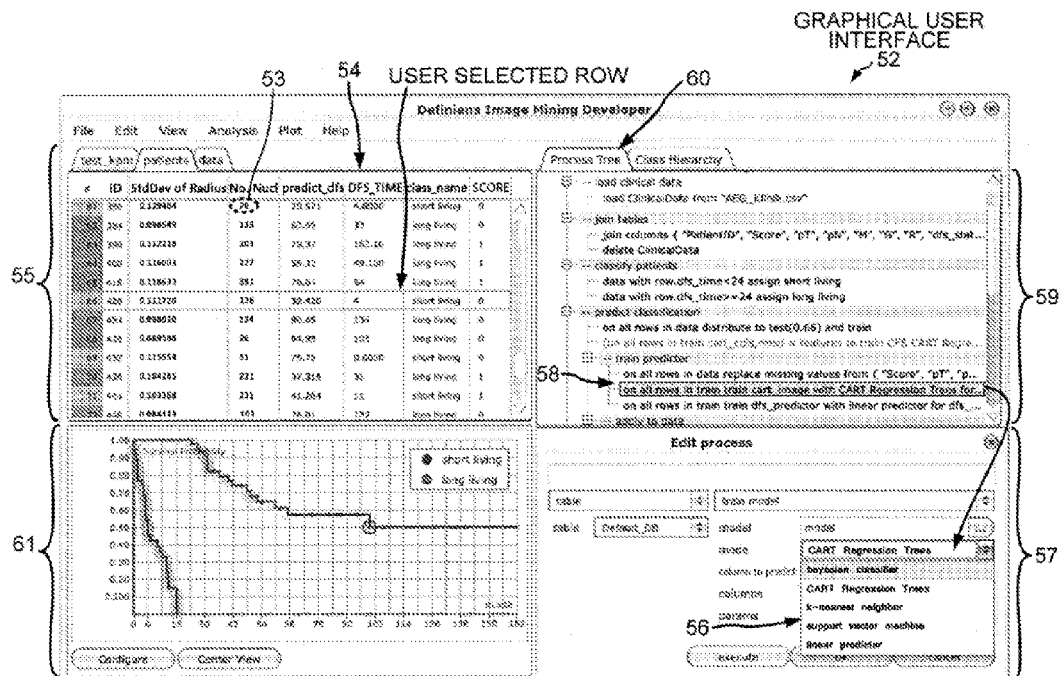
FIG. 8 is a screenshot of a graphical user interface that displays a list of selectable statistical methods for generating parameters to perform image analysis.
FIG. 9 is a screenshot of a graphical user interface that displays a new version of an image generated by analyzing the digital image using a new image analysis parameter.

FIG. 7 is a flowchart of yet another method by which system 10 displays the results of the analysis of bio-medical images in a table on a graphical user interface. The steps of the method of FIG. 7 are described in relation to a graphical user interface 52 as shown in FIG. 8.

In a step 47, a first image analysis value 53 is displayed in table 54 in a first pane 55 of graphical user interface 52. The first image analysis value 53 is generated by analyzing a digital image of a tissue slice using a first parameter. In the example of FIG. 8, the first image analysis value 53 indicates the number of nuclei in a portion of the digital image #380 as counted by the image analysis software after classifying and segmenting the digital image using the first parameter generated by a first statistical method. The image analysis program has counted 76 nuclei in the portion of image #380 that is being analyzed. Image #380 is associated with a slice of tissue taken from patient #61.

Similar to table 32 of graphical user interface 15, table 54 of graphical user interface 52 also has user selectable rows. The sixth row for patient #66 has been selected in the view of table 54 in FIG. 8. The user selectable row is marked with a color that corresponds to a classification of the digital image of the tissue slice provided by patient #66. In the column listing the patient number, each selectable row has a color that classifies the image as signifying either a short living or a long living patient. The user selected row the has a lighter color that classifies the image for patient #66 in the class "short living".

In step 48, a list 56 of selectable statistical methods is displayed in a second pane 57 of graphical user interface 52. Examples of statistical methods used to generate image analysis parameters include generating a decision tree, generating a linear regression plot, generating a support vector machine, generating a Bayes classifier, determining the k-nearest neighbor and determining a linear predictor. List 56 includes the first statistical method used to generate the first parameter as well as a second statistical method. In this example, a regression decision tree method ("CART Regression Trees") is the first statistical method used to determine the first parameter in a step 58 of the image analysis process. Graphical user interface 52 includes a pane 59 that shows the process tree 60 with the steps by which image analysis of the digital image is performed. The steps describe the program flow of the image analysis software. For each step of the image analysis process, graphical user interface 52 permits the user to substitute alternative statistical methods to calculate threshold parameters without having to define an entirely new process. In one example, the statistical method calculates parameters to generate a decision tree used to classify and segment objects in the digital image. The first parameter is a decision threshold applied at decision points in the decision tree. The statistical method can also use the results of earlier image analysis to generate parameters used in subsequent classification and segmentation. The statistical method can use the first image analysis value 53 to generate parameters for analyzing the digital image in subsequent steps. For example, depending on the number of nuclei in a portion of the image as determined by the image analysis program in a preliminary classification, the statistical method sets a threshold parameter used to classify and segment objects in the digital image in subsequent steps.

In a step 49, a second parameter is computed using a second statistical method after the user has selected the second statistical method. In FIG. 8, the user is selecting the highlighted second statistical method "bayesian classifier". The second threshold parameter is then determined using the Bayesian classifier method.

In a step 50, a second image analysis value is displayed in table 54 after the user has selected the second statistical method. The image analysis program generates the second image analysis value by analyzing the digital image using the second parameter determined using the second statistical method. For example, image analysis using the second parameter might determine that there are more than 76 nuclei in the portion of the image being analyzed.

In a step 51, a new version of the digital image is displayed in a third pane 61 of graphical user interface 52 after the user has selected the second statistical method. The new version of the digital image is generated by analyzing the digital image using the second parameter. For example, the new version of the digital image might show more than 76 segmented nucleus objects in the portion of the image being analyzed.

FIG. 8 does not illustrate the new version of the digital image in third pane 61. Instead, FIG. 8 shows Kaplan-Meier curves in third pane 61 representing the predicted disease free survival times of the patients whose biopsy tissue samples are being analyzed. For each selectable row marked in the patient # column having a lighter color to signify predicted short living, there is a point along the lower "short living" curve in the Kaplan-Meier plot. The image analysis program, however, allows the user to define third pane 61 or another pane for displaying the most recent segmented version of the digital image that is being analyzed.

FIG. 9 shows another embodiment of graphical user interface 52 that displays a new version 62 of the digital image in third pane 61. New version 62 of the digital image is generated by analyzing the digital image using the second parameter. FIG. 9 also shows the prior version 63 of the digital image that was generated by analyzing the digital image using the first parameter. For example, the first image analysis value indicates the largest contiguous stained area and is generated by analyzing the digital image using the first parameter determined using the first statistical method. The second image analysis value is generated by analyzing the digital image using the second parameter determined using the second statistical method. The second image analysis value would be larger than the first image analysis value because the segmentation of the new version 62 of the digital image has generated larger stained objects than in the prior version 63.

In another example, the first and second parameters are segmentation thresholds. The first and second statistical methods can be aggregation methods that compute the parameters by determining an average value, determining a standard deviation value, determining an absolute deviation value, or determining a quantile value. In the example of FIG. 9, the stained objects in prior version 63 of the digital image could be classified and segmented based on the average radius of the objects, whereas the stained objects in new version 62 of the digital image could be classified and segmented based on the standard deviation of the radius of the objects (see 64).

In another embodiment, the image analysis program is used to generate biomarkers that predict a clinical endpoint of a patient. Data mining techniques are combined with image analysis to achieve context-driven image mining. Data mining steps are incorporated into the software tool that performs the image analysis. An image-based biomarker is a predetermined set of image analysis features weighted and combined in a predetermined manner to provide an indication of a clinical endpoint. Examples of clinical endpoints include a patient's overall survival time (OS), the disease free survival time (DFS), the probability that a treatment, therapy or drug will be successful or effective, the probability of getting a specific disease, the disease recurrence probability, the patient's disposition to having a heart attack or stroke, or the patient's life expectancy.

The computer language is the foundation of the image analysis software that performs data mining. For example, the image analysis software generates more accurate Kaplan-Meier curves of disease-free survival times (DFS). In a first processing round, data mining results are produced from the image analysis results. Certain items of the data mining results (e.g., a point in a scatter plot or a marker in a Kaplan-Meier curve) are classified as being outlier data that does not represent a good correlation between the data mining result and an observed clinical endpoint, such as the disease-free survival time (DFS). The image analysis program automatically triggers new image analysis algorithms depending on the classification of the outlier items in the data mining result. Those new image analysis algorithms range from applying completely new segmentation and classification algorithms to simply modifying or extending the features that are exported into the table. In both cases, the table of output data is modified and thus results in a modified data mining output. The data mining output then leads to an automatic restructuring of the table in a way that different parts of the table are exposed to different data mining algorithms (or the same algorithms with different parameters). In this way, the software tool automatically optimizes data mining results.

Image analysis has one main goal: to end with a number, score or diagnosis. Achieving a segmentation of an image and a classification of the segments is a prerequisite for obtaining the number, score or diagnosis as opposed to the ultimate goal. There are two different use cases for image analysis.

Type 1. In the first type of image analysis, an individual case is important. The analyzed images relate to a single individual (e.g., patient, mouse, specific cell culture, or specific zebra fish culture). The individual case is evaluated, perhaps also in combination with other data, resulting in a score or a diagnosis. The result can be information represented by a table. Those results can be incorporated into a decision support system, such as a clinical decision support system, a drug development support system, or a translational research support system. The goal of this first type of image analysis is to learn something about the individual case.

Type 2. In the second type of image analysis, a collection of cases is important. The analyzed images relate to a large number of individuals. The individual results are less important than the collective content of the images. The results of the image analyses (individual scores or tables) are combined into one table called a meta-table. In most cases, additional data are also incorporated into this meta-table. The additional data can be a wide variety of data about the individuals (e.g. patients, mice, specific cell cultures, specific fish cultures) to which the images relate. For example, the meta data can include a patient's age and weight, family history, known diseases and intolerances, DNA profile, blood values, whether the patient smokes and whether the patient breast fed her babies.

For both types of image analysis, the additional step of data mining follows. The image analysis program searches for patterns and correlations in the comprehensive data set (table of type 1 or 2). For additional details on searching for patterns and correlations relating to type 1 tables, see U.S. patent application Ser. No. 12/799,709 entitled "Image-Based Patient Profiles," filed on Apr. 29, 2010 and published as U.S. Pat. Pub. No. 2011/0268331, which is incorporated herein by reference. There are different forms for visualizing patterns and correlations. The image analysis disclosed herein involves the alternation of classification and segmentation. A specific classification triggers a specific segmentation algorithm. This means that the classification of the analysis result is used as a hint for triggering a new analysis. In this manner, the quality of the analysis is optimized in an iterative manner. After the image analysis comes to an end, several features of image objects are exported into tables. Those features are generally of a statistical nature. After the application of data mining algorithms, data mining results are produced. Within those results, hints are again generated as to which new additional data mining algorithms should be applied, or which new structures of the table should be implemented, or which new image analysis algorithms should be applied (perhaps only to certain types of images), or which new image features should be exported into the table. A large number of image features are exported into the table, and the data mining procedure selects the relevant ones. There is, however, a computational problem as the possible combinations of new features quickly become too large to calculate. Whenever the number of permutations gets too large, it is advantageous to collect hints for limiting the permutations. Collecting the hints is called "context driven analysis," which heretofore has been applied only to image analysis and now is also being applied to data mining of the results of the image analysis, which we call "Image Mining." Thus, Image Mining is the unification of image analysis and data mining, and the software tool performs context-driven image mining.

The image analysis program performs "context-driven image mining" by combining image analysis and data mining in a unified form such that the individual results of the data mining are classified, or parts of the data tables are classified and structured. Those classifications are then used to perform modified and additional image analysis, as well as modified and additional data mining with the results of the image analysis.

Figure 10:
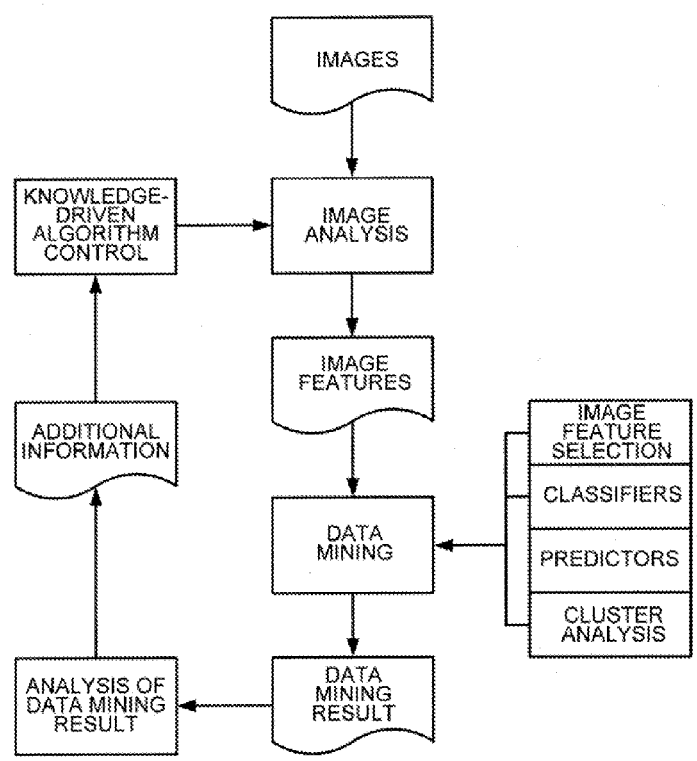
FIG. 10 is a diagram of a feedback loop that feeds image analysis results back into the image analysis steps to refine the image analysis.

FIG. 10 shows a feedback loop in which image analysis and the results of the analysis are fed back by knowledge-driven algorithms into the image analysis step to refine the image analysis. In each subsequent iteration of the loop, image analysis can extract additional image parameters and continue processing the image. Subsequent processing can look for new structures that were not analyzed during the first run. In subsequent steps, the analysis algorithms may be applied only to a portion of the image. Algorithms of the image analysis program control the iteration loop and can use knowledge-driven and local adaptive processing based on hierarchical semantic networks. The control algorithms stop the iteration loop when predetermined conditions are met, such as a threshold being reached or after a certain number of iterations.

In one example of the iterative feedback-loop processing, object-based image analysis first generated high-level objects and low-level objects. For example, the low-level objects include nuclei, lumina, cell membranes and cytoplasm. The high-level objects include glands, necrotic areas, tumor regions and epithelia tissue. High-level objects are made up of low-level objects. For example, glomeruli are organelles made up of nuclei, lumina and other cellular structures. Each of the objects has a multitude of properties (so-called "image features") that can be measured and evaluated for data mining purposes.

A number of predefined image features are extracted from each of a plurality of medical images. Due to the multitude of image features associated with the multitude of image objects, the image features used for image-based data mining ("image mining") are limited upfront so that the available processing resources can perform the required calculations of the iterative feedback-loop processing. Nevertheless, the number of features used in the feedback-loop processing can be larger than if the calculations for the image mining were performed in a straight shot without the feedback loop.

Consider a simple exemplary image analysis performed in a linear flow compared to being performed with the novel iterative feedback-loop processing. Even a simple medical analysis results in a multitude of image features. For example, five high-level objects (tumor, stroma, necrotic areas, inflammations) are analyzed on five hundred images of tissue with tumor structures. For each high-level object, three lower-level objects (nuclei, lumina, other cell compartments) are analyzed, each having eight different subtypes. This simple case covers only a small number of the typical parameters that are considered by a pathologist investigating breast cancer tissue. And complex clinical studies can involve thousands of patients with several images per patients. In the simple case, four measurements are made per low-level object such as area, staining intensities of two stains and shape distribution parameter. Eight measurements are made per high-level object, and four additional measurements characterize subtypes of objects. Consequently, the simple case requires twelve basic image features, thirty-two image features for the objects and sixteen image features for the subtypes of objects. These sixty image features already pose a significant challenge to one-shot processing of the data mining algorithms. But if objects are eliminated from the model, then image parameters based on these neighboring objects will be zero and will lead to poor results.

The novel iterative feedback-loop processing method, however, starts with simple high-level image analysis that is significantly faster than a robust analysis performed all at once. In this way, a first subset of image features is extracted from each image. The data mining algorithms then evaluate the image analysis results and group the images based on the results. In a second iterative processing step, the images are analyzed based on their image features. For example, those regions of the images are analyzed more intensively that have features indicating tumor cells or inflammation. If data mining of the results of the first iteration showed two types of results, then the images are separated for two groups of patients. Specialized image analysis algorithms are performed on each group of images and need not be performed on all of the images. Segmentation and classification tasks are split up into subprocesses that must process a smaller number of model parameters using a more consistent set of variables from a smaller portion of the images.

In one embodiment, an image-based biomarker is developed that correlates the data mining results of the image analysis to a clinical endpoint. The magnitude of the biomarker indicates how best to draw a conclusion from the image analysis results. The biomarker is based on feature vectors that describe regions of interest in medical images of a patient, as well as meta data properties. As indicated above, meta data properties comprise the patient's age, sex, family history, blood values, or genetic profile, and results from prior examinations. The feature vectors describe objects of a data network and can be defined as Euclidian vectors. For this embodiment based on the analysis of medical images, the feature vectors are denoted as "image features." Thus, the image features describe various properties of classified objects in the medical images. Examples of image features include: average size of the nucleus of a cancer cell, the staining intensity of a membrane compared to the cytoplasm, the percentage of inflammation of a class of cells, the density of tumor cells and the number of epithelial cell layers.

Figure 11:
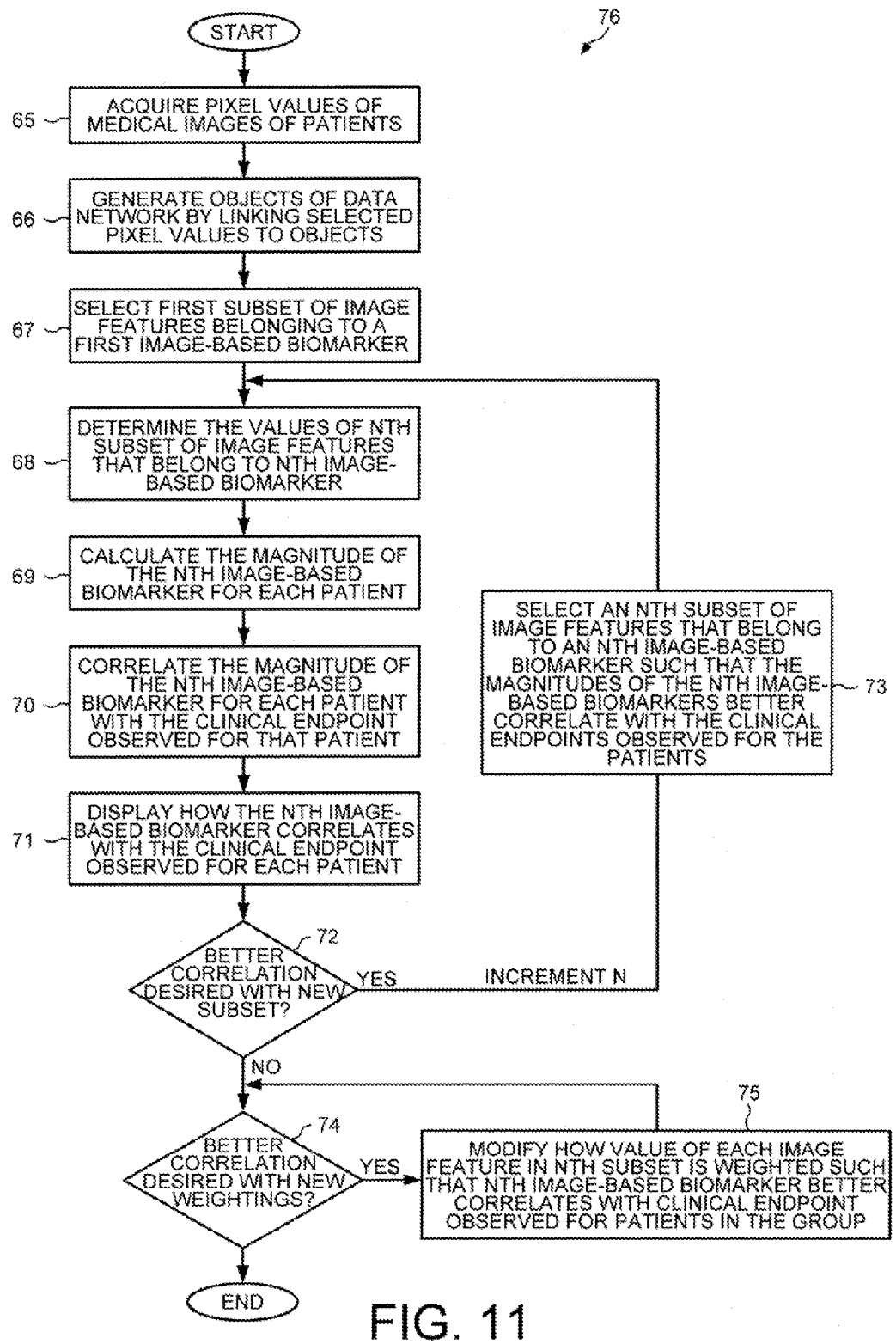
FIG. 11 is a flowchart of steps for analyzing medical images of patients to generate an image-based biomarker.

FIG. 11 is a flowchart illustrating steps 65-75 of a method 76 for analyzing medical images of patients to generate an image-based biomarker whose magnitude correlates to a clinical endpoint that was observed for the patients whose medical images were analyzed. The image-based biomarker can be used to predict the clinical endpoint of other patients whose clinical endpoints have not yet been observed. The steps of method 76 are described in relation to the images and screenshots depicted in FIGS. 11-16.

In a first step 65, pixel values are acquired from medical images of a group of patients. In one example, images were acquired from three hundred ninety biopsy tissue cores taken from one hundred thirty-two patients with esophagogastric cancer. The biopsy tissue was stained for the protein called human epidermal growth factor receptor 2 (HER2/neu) using antibody clones. The HER2 protein promotes the growth of cancer cells. Immunohistochemistry (IHC) was performed to determine HER2/neu protein expression. Method 76 is thus used to generate an image-based biomarker that correlates to the disease free survival time (DFS) and the overall survival time (OS) of patients with a high risk factor for acquiring HER2-positive esophagogastric cancer. In about one of every five cancers, the cancer cells make an excess of HER2 due to a gene mutation. HER2-positive cancer tends to be more aggressive than other types of cancer. However, treatments that specifically target HER2 are very effective, including trastuzumab (Herceptin) and lapatinib (Tykerb).

The manual scoring of biopsy tissue by a pathologist to estimate clinical endpoints was compared to the performance of method 76. The tissue micro arrays of FIG. 3 were used. FIG. 3 shows one of three tissue micro arrays on which the three hundred ninety biopsy tissue cores were placed. Tissue micro array 30 includes two hundred twenty-seven biopsy tissue cores taken from some of the one hundred thirty-two esophagogastric cancer patients. The tissue cores in box 31 are shown in more detail in FIG. 13. To compare the performance of method 76 with clinical endpoints estimated by a pathologist, a pathologist scored each biopsy tissue core as 0, 1+, 2+, or 3+. A score of 0 or 1+ is negative for the presence of the HER2 protein. A score of 2+ is weakly positive (using IHC), and 3+ is positive.

In step 66, objects of a data network are generated for each of the medical images by linking selected pixel values to selected objects according to a class network and a process hierarchy. For example, objects are generated for all of the cells and cell parts in cancerous regions of interest in the tissue on the tissue micro arrays.

Figure 12:
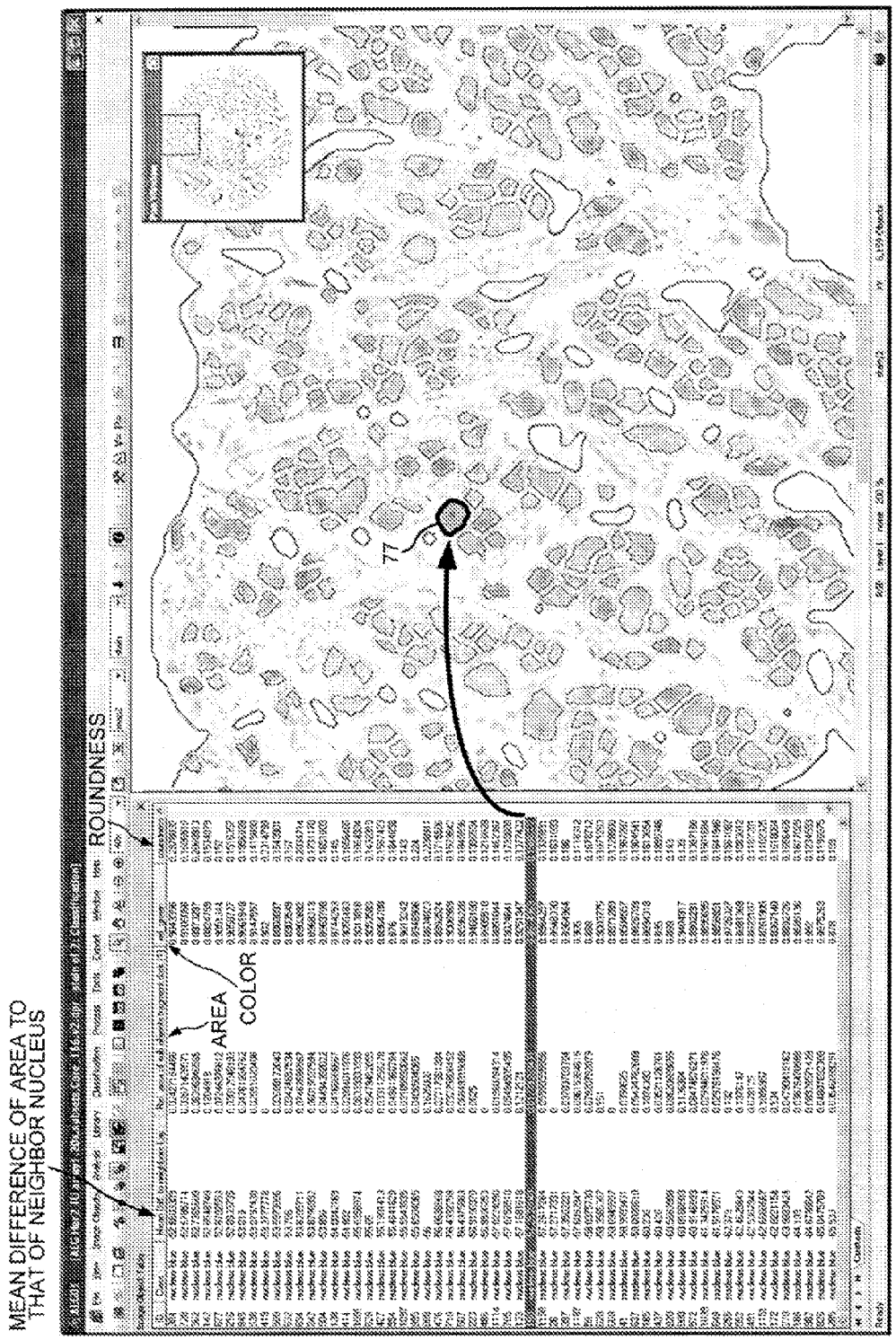
FIG. 12 is a screenshot showing objects generated from one part of the medical images of FIG. 3.

FIG. 12 is a screenshot generated by the image analysis program showing the objects generated in just one part of the digital image of one biopsy tissue core. On the left is a table listing four of the many image features of the objects that are segmented in the digital image on the right side of the graphical user interface. The table lists the values of the four image features: (i) mean difference of area to that of neighbor nucleus, (ii) area of nucleus, (iii) color of nucleus, and (iv) roundness of nucleus. An object 77 is highlighted in the digital image on the right side of the screenshot. Object 77 represents a nucleus in the biopsy tissue. The values of the four image features for object 77 are highlighted in the list on the left side of the screenshot. The highlighted values of the four image features for object 77 are: −57.25, 0.01779, 0.897 and 0.1596.

FIG. 13 is another screenshot of the graphical user interface of the image analysis program. The digital image on the right side of the screenshot is a more detailed view of box 31 shown in FIG. 3. Each of the biopsy tissue cores has been segmented as an object of a data network. The substructures in each of the biopsy tissue cores have also been segmented and classified. The digital image of the lower right biopsy tissue core in box 31 has been placed in a matrix of tissue cores on the left side of the screenshot. The plurality of image features for the objects in each tissue core are then accessible by clicking on the appropriate tissue core in the matrix.

In step 67, a first subset of image features is then selected from the multitude of possible image features that can make up a first image-based biomarker. For example, the first image-based biomarker correlates the image features to the overall survival time (OS) of each patient.

In step 68, the values of the subset of image features that belong to the image-based biomarker are determined. Method 76 involves an iterative process of improving upon the correlation between an image-based biomarker and a clinical endpoint, such as the overall survival time. Thus, in the first iteration of step 68, the value of each of the first subset of image features of objects generated using object-oriented image analysis is determined, where the first subset of image features belongs to the first image-based biomarker.

Figure 14:
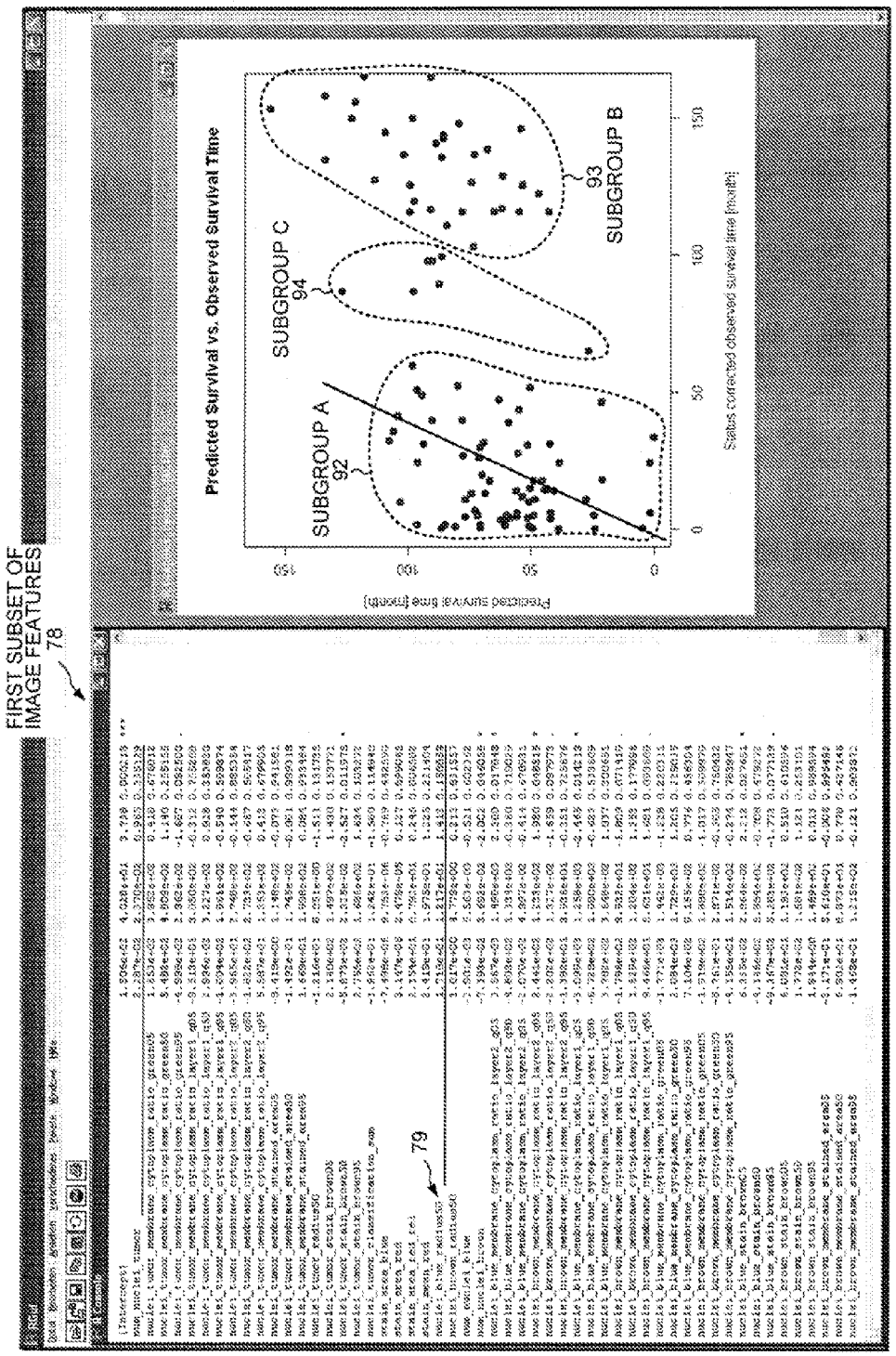
FIG. 14 is a screenshot with a list of image features that make up an image-based biomarker.

FIG. 14 is a spreadsheet generated by the image analysis program that lists fifty-four image features in a first subset 78 of image features that make up the first image-based biomarker (CORE_METADATA.OS_TIME) that correlates the image features to the overall survival time (OS) of each patient. For example, the beginning image features in subset 78 include: (1) number of nuclei, (2) amount of membrane with a green stain intensity of 5% of the cytoplasm stain intensity, (3) amount of membrane with a green stain intensity of 50% of the cytoplasm stain intensity, (4) amount of membrane with a green stain intensity of 95% of the cytoplasm stain intensity, (5) amount of membrane with a stain intensity of 5% of the cytoplasm layer 1 stain intensity, (6) amount of membrane with a stain intensity of 50% of the cytoplasm layer 1 stain intensity, and (7) amount of membrane with a stain intensity of 95% of the cytoplasm layer 1 stain intensity. Subset 78 also includes the image feature 79 (nuclei_blue_radius50) which indicates the average length of the radius of the blue stained nuclei.

Figure 15:
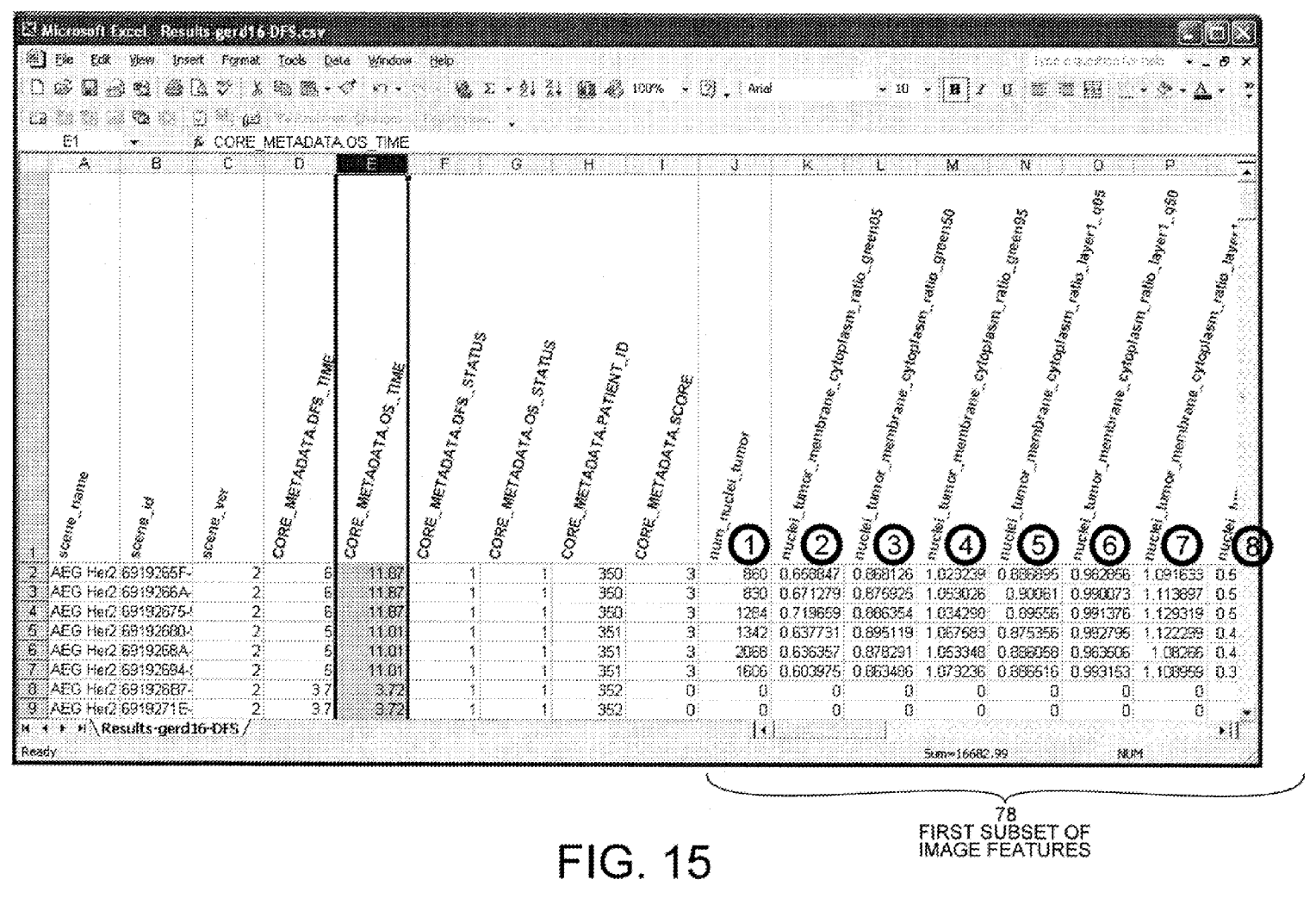

FIG. 15 is a spreadsheet generated by the image analysis program that lists the values of the image features for each of the identified objects, in this case the objects in the biopsy tissue cores in the matrix in FIG. 13. Each of the biopsy tissue cores is associated with the patient from which it was taken. The first image-based biomarker (CORE_METADATA.OS_TIME) is highlighted in FIG. 15. The spreadsheet lists the values of the first eight of the image features from first subset 78. The spreadsheet indicates that the first biopsy tissue core has 860 nuclei, the second tissue core has 830 nuclei, and the third tissue core has 1284 nuclei.

In step 69, the magnitude of the first image-based biomarker is calculated for each patient using the values of image features obtained from the biopsy tissue cores obtained from that patient. In a first embodiment, calculating the magnitude of the image-based biomarker involves weighting each value of each image feature in first subset 78 and then summing all of the weighted values. The spreadsheet of FIG. 14 shows how each of the fifty-four image features is weighted. For example, the image feature indicating the number of nuclei has a weighting of 0.335129, whereas the weighting of feature 79 (nuclei_blue_radius50) is 0.158859. The magnitude of the first biomarker is calculated by multiplying the value of each of the fifty-four image features times the corresponding weighting, and then summing the products. For the first image-based biomarker that correlates the image features to the overall survival time (OS) of each patient, the magnitude of the biomarker is converted into an associated number of months indicating the survival time.

Figure 16:
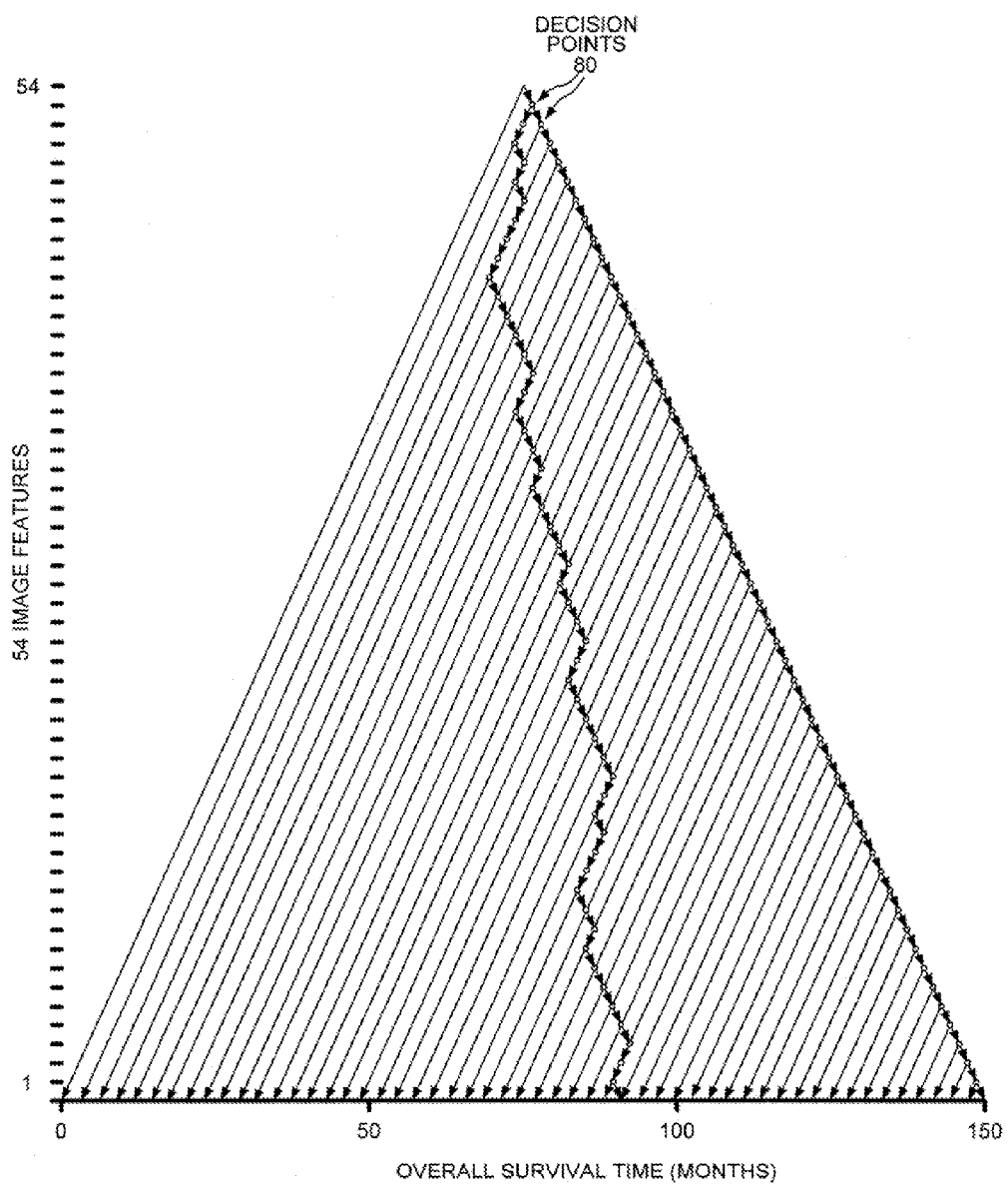
FIG. 16 is a diagram of a decision tree used to determine the magnitude of the image-based biomarker.

FIG. 16 illustrates a second embodiment of how the magnitude of the image-based biomarker is determined. The magnitude of the image-based biomarker is determined by performing a decision tree analysis with each feature in first subset 78 to generate a predicted clinical endpoint for each patient. In the second embodiment, a decision is made based on the value of each image feature as to whether the patient is likely to have a longer life or a shorter life. At each decision point 80 of the decision tree, the analysis takes the path of a longer or shorter overall survival time depending on whether the value of the image feature exceeds a predetermined threshold value. To simplify the illustration of FIG. 16, only the decision points 80 on the outer path of a longer life as well as along one exemplary inner path are shown. In the exemplary decision tree of FIG. 16, the amount of a longer or shorter overall survival time added at the decision point for each image feature is the same. However, weightings similar to those listed in FIG. 14 can be applied to each image feature by adding weighted increments of survival time at each decision point.

In step 70, the magnitude of the first image-based biomarker for each patient is correlated to the clinical endpoint observed for that patient. For the first image-based biomarker (CORE_METADATA.OS_TIME) that predicts overall survival times (OS), the number of months of overall survival time predicted for each patient is correlated to the actual time in months that each patient was observed to survive.

In step 71, how the first image-based biomarker correlates with the clinical endpoint observed for each of the patients in the group of one hundred thirty-two esophagogastric cancer patients is displayed on a graphical user interface generated by the image analysis program.

A screenshot of the graphical user interface 15 generated by the image analysis program that includes a scatter plot is shown in FIG. 4. In one embodiment, the x axis represents the observed survival time, and the y axis represents the survival time predicted by the image-based biomarker. The screenshot of FIG. 4 also includes a list in the upper left showing the values of the image features similar to the list of FIG. 15. The screenshot also includes an image on the right side showing one of the biopsy tissue cores from the tissue micro array 30 of FIG. 3.

A scatter plot of survival times is also included on the right side of FIG. 14. The scatter plot of FIG. 14 correlates the overall survival times predicted by the first image-based biomarker to the overall survival times observed for each of the patients in the group of one hundred thirty-two esophagogastric cancer patients. The correlation of the magnitude of the biomarker to the observed survival times is better the closer the points are grouped around a line that emanates from the intersection of the x and y axes.

In a decision step 72, the user of the image analysis program decides whether a better correlation is desired between the survival times predicted using the first biomarker and the observed survival times. Considering that all of the points in the scatter plot of FIG. 14 are not located close to any line that emanates from the intersection of the x and y axes, the user determines that a better correlation can be achieved with a new biomarker made up of a different subset of image features. Method 76 of FIG. 11 is now used to improve the correlation between the observed clinical endpoints and a second image-based biomarker.

In a step 73, a second subset of image features is selected that belong to the second image-based biomarker such that the magnitude of the second biomarker for each of the patients better correlates with the clinical endpoint observed for each patient. The second subset can be selected by adding new image features to first subset 78 and/or by deleting other image features. Image features can be added that relate to the relationships between objects as opposed to simply the properties of the objects themselves. For example, the second subset can include the radius of each nucleus as well as the distance to the nearest neighboring nucleus. Steps 68-71 are then repeated for the second image-based biomarker using the second subset of image features. New biomarkers are generated using new subsets of image features until the user decides not to attempt to achieve a better correlation with a different subset of image features.

In a decision step 74, the user of the image analysis program decides whether a better correlation between predicted and observed survival times can be achieved by calculating the magnitude of the nth biomarker using different weightings of the values of the nth subset of image features.

In a step 75, the manner in which the value of each of the image features in the nth subset is weighted is modified such that the magnitude of the nth biomarker better correlates with the observed clinical endpoints for the patients in the group. The weightings of the image features used to calculate the magnitude of the biomarker are modified until the user decides that a better correlation is not required.

Figure 17:
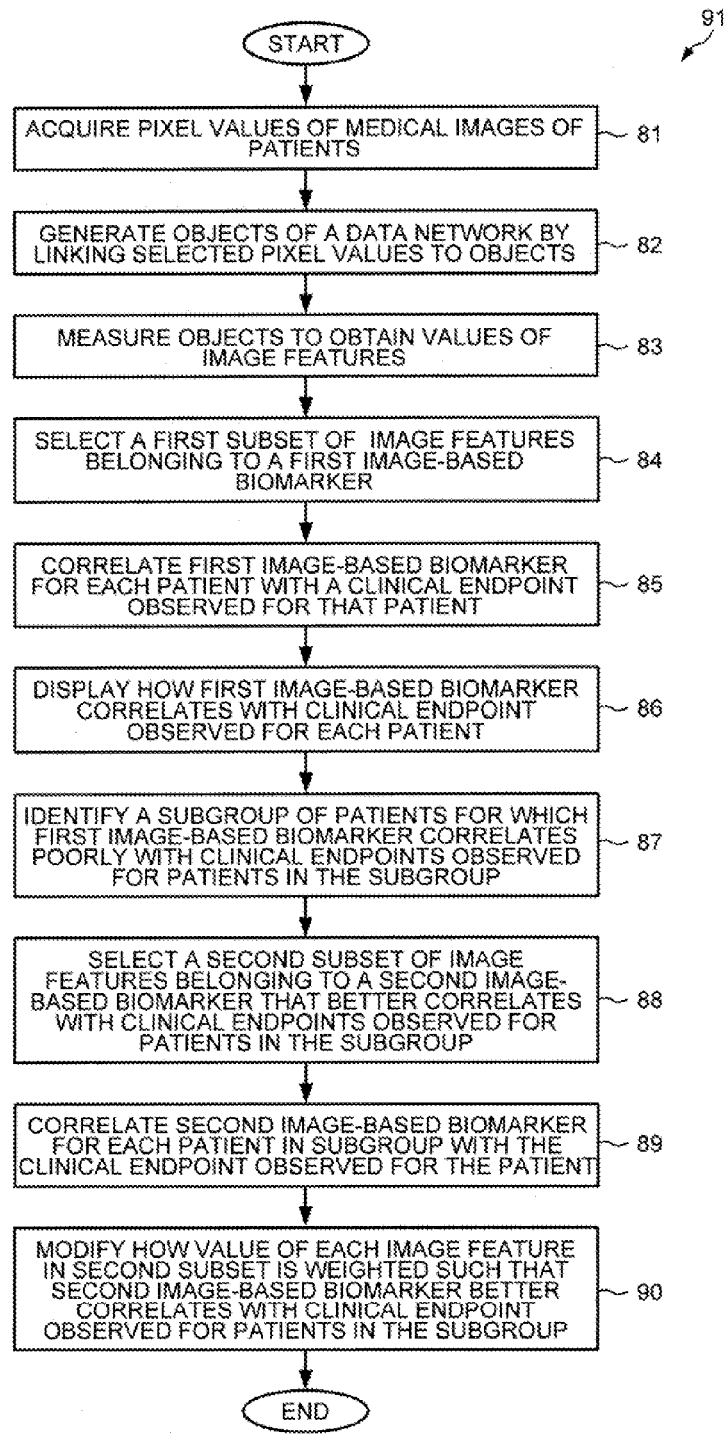
FIG. 17 is a flowchart of steps for analyzing medical images to generate separate image-based biomarkers for two groups of patients whose observed clinical endpoints correlate differently with the biomarkers.

FIG. 17 is a flowchart illustrating steps 81-90 of a method 91 of analyzing medical images of patients to generate separate image-based biomarkers for two groups of patients whose observed clinical endpoints correlate differently with a single biomarker generated using the same set of image features. Method 91 is used to segregate the patients into subgroups that each show a better correlation with a different biomarker generated using different image features.

In a first step 81, pixel values are acquired from medical images of a group of patients. Regions of interest in the digital images are analyzed. For example, the tumor cells in immunohistochemistry (IHC) stained digital pathology slides are identified, segmented and analyzed for HER2 protein expression.

In a step 82, objects of a data network are generated for each of the medical images by linking selected pixel values of the images to selected objects according to a class network and a process hierarchy.

In a step 83, the objects are measured to obtain a value for each of a plurality of image features. For example, the image features include the number of tumor cells, the average staining intensity, the average radius of tumor cells, and the substructure of tumor nuclei image objects. Image features also include the relationship between other image features, for example the standard deviation of the area of the nuclei of the tumor cells.

In a step 84, the image features of a first subset are selected that belong to a first image-based biomarker. For example, fifty-four image features are chosen from among the multitude of possible image features that can be obtained by measuring and analyzing the objects in the medical images. The magnitude of the first image-based biomarker is calculated by summing the weighted values of the image features in the first subset.

In a step 85, the magnitude of the first image-based biomarker for each patient is correlated with the clinical endpoint observed for that patient. In this example, the first image-based biomarker is correlated to the overall survival time (OS) and to the disease free survival time (DFS).

In a step 86, the image analysis program displays how the first image-based biomarker correlates with the observed clinical endpoint. In this example, the correlation is displayed in a scatter plot that plots the predicted overall survival time of each patient based on the value of the first biomarker compared to the observed survival time. An example of such a scatter plot is the graph at the right of FIG. 14. The correlation between the biomarker and the observed survival time is better the closer the points are grouped around a line the emanates from the intersection of the x and y axes. The scatter plot of FIG. 14 shows that not all points are grouped around any single line.

In a step 87, a subgroup of patients is identified for which the first image-based biomarker correlates poorly with the clinical endpoint observed for the patients in the subgroup. The scatter plot at the right of FIG. 14 shows three groupings of points. A subgroup A (92) of points to the left of the graph indicates a good correlation between the observed survival time and the survival time predicted by the first biomarker. A subgroup B (93) to the right of the graph represents patients who recovered from the disease and did not die of the disease. The first image-based biomarker correlates poorly with the observed survival times of the patients in subgroup B because the patients recovered from the esophagogastric cancer.

The first image-based biomarker also correlates poorly with the observed survival times of the patients in subgroup C (94). Each of the patients in subgroup C (94) represents an outlier for which the fifty-four image features of the first image-based biomarker do not provide a good indication of the overall survival time. For example, each of the patients in subgroup C is an outlier because the point plotting the magnitude of the first biomarker versus the observed survival time lies far away from the linear regression line through the center of the points of subgroup A.

In a step 88, a second subset of image features is selected that belong to a second image-based biomarker that better correlates with the clinical endpoints observed for the patients in subgroup C (94). Additional image features can be added to the second biomarker, or some image features can be removed. For example, if the first biomarker used the average staining intensity of tumor cells, the second biomarker uses the relative staining intensity of the membrane compared to the cytoplasm of the tumor cells. Thus, a different subset of image features is used for the patients in subgroup A (92) than is used for patients in subgroup C (94). The magnitude of the second biomarker is then determined for each patient in subgroup C using the image features in the second subset.

In a step 89, the magnitude of the second image-based biomarker for each patient in subgroup C is correlated with the clinical endpoint observed for each patient. The correlation is then displayed in a new scatter plot for just the patients in subgroup C.

In a step 90, the manner in which the value of each of the image features in the second subset is weighted is modified such that the magnitude of the second image-based biomarker better correlates with the observed clinical endpoints for the patients in subgroup C (94). Once the user of the image analysis program is satisfied with the correlation between the image-based biomarker and the observed clinical endpoint observed for the patients in subgroup C, the image features and weightings that make up the second biomarker are saved to the file system.

The second image-based biomarker is then used to predict the clinical endpoint in new patients whose clinical endpoints have not yet been observed and for whom the first image-based biomarker results in a magnitude that falls outside a predefined base range.

Figure 18:
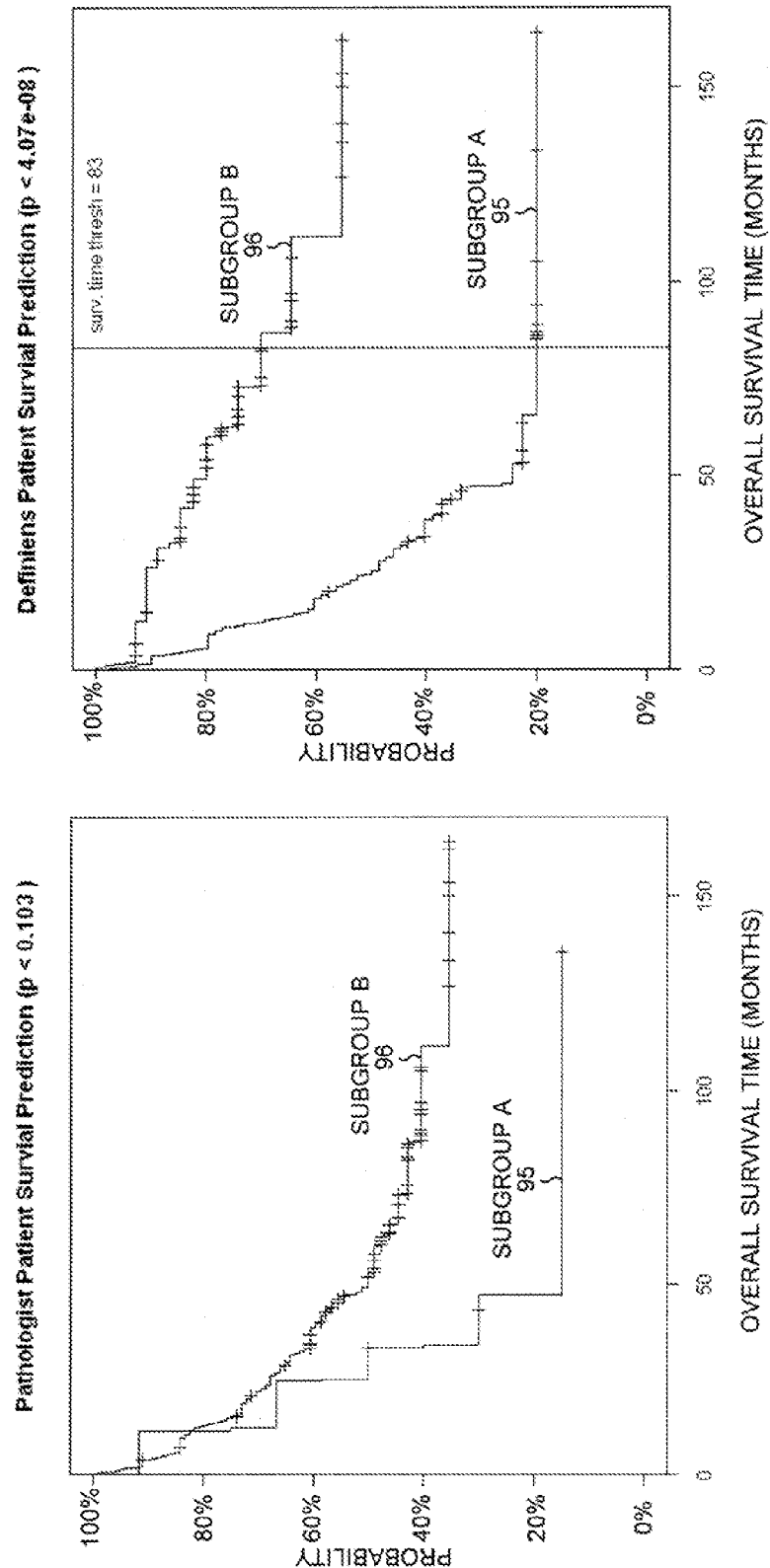
FIG. 18 is a Kaplan-Meier graph that shows overall survival times (OS) for two groups of patients.

FIG. 18 shows two Kaplan-Meier graphs that illustrate the ability of the image analysis program to distinguish between patients that belong to a main group of patients and an outlier subgroup of patients for which a first image-based biomarker does not provide a good correlation with observed clinical endpoints. As shown in FIG. 4, the image analysis program generates such Kaplan-Meier graphs. A Kaplan-Meier curve descends step-like over time and plots the percentage of the observed population still alive after a given period. For example, the lower curve of the Kaplan-Meier graph on the left side of FIG. 18 indicates that after about twenty-five months about fifty percent of the patients in a subgroup A (95) still survive. The upper curve indicates that after about one hundred months about forty percent of the patients in a subgroup B (96) still survive.

Two Kaplan-Meier curves can be compared to determine whether they differ statistically using a log-rank test or Wilcoxon's test. The "p value" indicates the probability of finding a difference between the two curves more extreme than the one observed even if the survival distributions of the two curves do not differ. If a predictor, such as an image feature used to generate a biomarker, results in a p value (comparing the results using the image feature and not using the image feature) of greater than 0.25, it is highly unlikely that the image feature will contribute anything to a biomarker that includes other image features.

In both Kaplan-Meier graphs of FIG. 18, the patients in subgroup A (95) along the lower curve correspond to patients in subgroup A (92) of FIG. 14 whose reduced overall survival time (OS) due to esophagogastric cancer correlates well with a baseline image-based biomarker. The patients in subgroup B (96) along the upper curve correspond to patients in subgroup B (93) of FIG. 14 who recovered at least partially from esophagogastric cancer and may have died from other causes.

The Kaplan-Meier graphs of FIG. 18 show that the image analysis program provided a better segmentation into two subgroups of patients exhibiting different survival characteristics. The p value separating the curves of subgroups A and B was $4.07 \times 10^{-8}$ when the patients in subgroup A (95) were identified using method 91 and the survival times were predicted using a second image-based biomarker. The p value separating the curves of subgroups A and B, on the other hand, was 0.103 when the patients in subgroups A and B were identified by a pathologist scoring biopsy tissue cores obtained from the patients. The patients in subgroup B (96) in the graph on the left were those patients whose tissue cores were scored by the pathologist as 0, 1+ or 2+. The patients in subgroup A (95) in the graph on the left were those patients whose tissue cores were scored by the pathologist as 3+, a positive score for the presence of the HER2 protein. By segmenting patients into groups for which a particular set of image features better correlated to the observed survival times of test subgroups of patients, the image analysis program can better predict the survival time of individual patients for which the survival time is not yet known.

Figure 19:
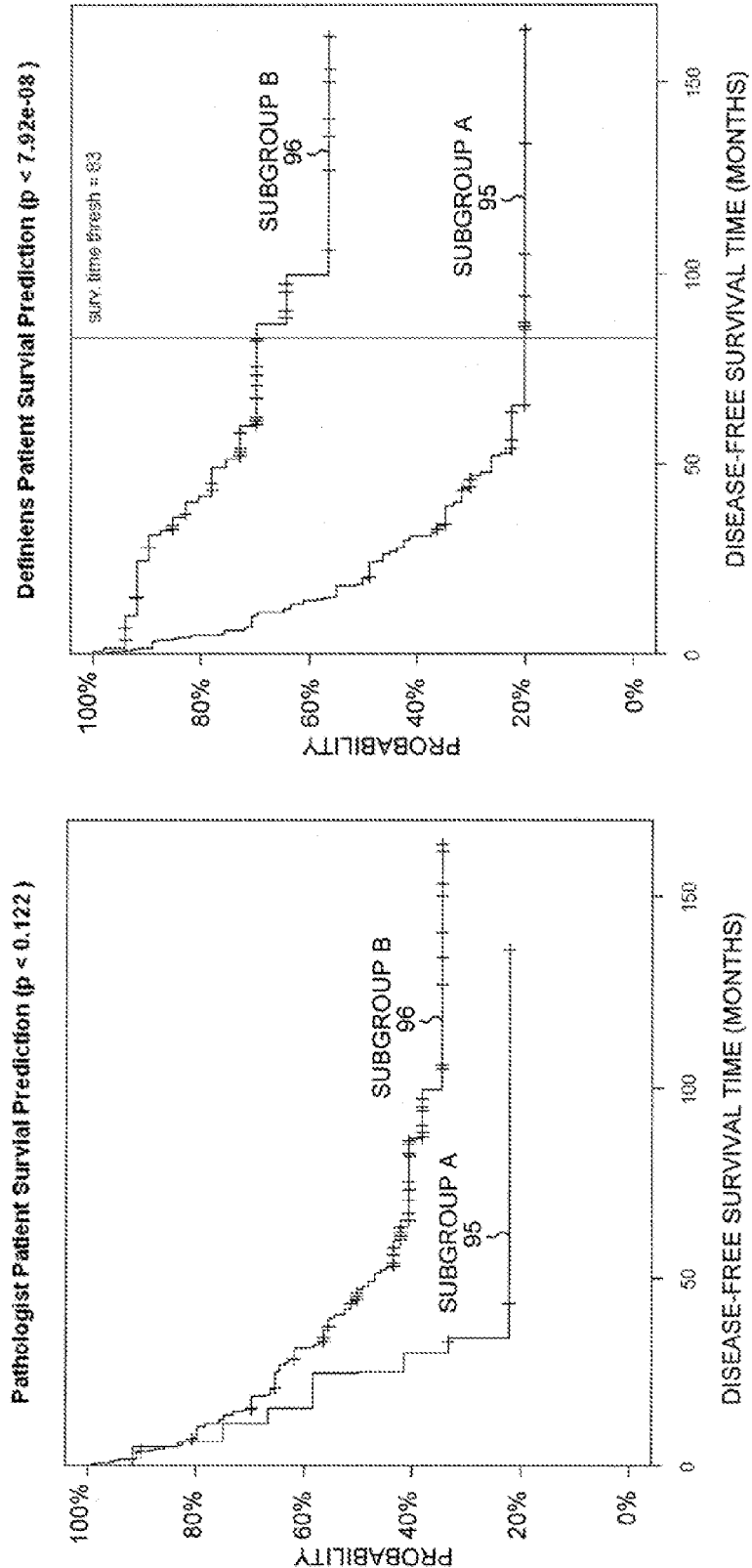
FIG. 19 is a Kaplan-Meier graph that shows disease-free survival times (DFS) for the two groups of patients.

FIG. 19 shows two Kaplan-Meier graphs that are similar to the graphs of FIG. 18 except that the curves represent the disease-free survival time (DFS) instead of the overall survival time (OS). The p value for the survival predictions of the two subgroups using method 91 performed by the image analysis program is much smaller than the p value obtained by a pathologist scoring the tissue cores.

In yet another embodiment, an image-based biomarker is developed especially for medical images acquired by a specific imaging device, such as a computed tomography (CT) device, a magnetic resonance imaging (MRI) device, or a positron emission tomography (PET) device. For example, a physician identifies malignant cells in the breasts of test patients by using microscopy to analyze biopsy tissue cores. PET scans are then taken of the test patients, and the locations in the patients' breasts from where the biopsies were taken are determined. Then a PET-specific image-based biomarker is developed that marks the objects in the vicinity of where the biopsy tissue cores were taken. Using method 76, a subset of image features and the weightings of those features are modified to arrive at the PET-specific image-based biomarker whose magnitude is large for the malignant cells around the biopsy locations but small for other objects in the PET scans. The PET-specific image-based biomarker can then be used for new patients to identify malignant cells in PET scans of their breasts. A new patient need not experience the discomfort of a biopsy in order to determine whether a suspicious mass in her breast is malignant. Using method 76, the experience of physicians at interpreting medical images acquired using one type of imaging device can be used to identify objects in medical images acquired using another type of imaging device.

In yet another embodiment, a custom biomarker is developed for a specific object in a region of interest in a medical image. For example, a physician identifies a "suspicious mass" in a medical image of a breast (a mammogram) of a particular patient. The image analysis program is then used to generate a custom image-based biomarker that specifically marks the suspicious mass. Using method 76, a subset of image features and the weightings of those features are modified to arrive at the custom image-based biomarker whose magnitude is large for the suspicious mass but small for other objects in the region of interest. Then a database of medical images is searched to find objects in mammograms of other patients that are also marked by the custom image-based biomarker. The physician then checks the medical records to determine whether the objects marked by the custom image-based biomarker were known to be malignant.

One such custom biomarker for detecting suspicious mass lesions in mammograms was developed based on 1024 images acquired from three hundred three different patients. Five different segmentation routines were performed on the images after a preprocessing step involving scaling the image size and conforming pixel gray values from different manufacturers' conventions. Because this segmentation produces a large number of objects, a pre-classification is applied that excludes non-plausible mass lesion objects by means of size, contrast and position criteria. A training database includes the image features of the remaining objects together with related patient meta-data (e.g., age). The training database also includes mammograms annotated by physicians that are used to test the performance of the custom biomarker.

Correlations between the annotated suspicious objects and the image features of the segmented objects are used to develop the custom biomarker for suspicious mass lesions. The goal is to define a custom biomarker that selects from all segmented objects more than 80% of the objects whose size and position are very similar to those of the annotated objects. Thus, the custom biomarker should achieve a hit rate of greater than 80%. The second goal is to minimize the number of objects marked by the biomarker that do not correspond to an annotation. Thus, a hit rate of more than 80% should be achieved at the same time that the number of false positives is minimized.

This goal is achieved in two ways. First, only those image features are selected that are best suitable for the custom biomarker. Second, the image features are combined in a mathematical logical expression in order to mark objects as being suspicious or not suspicious. Alternatively, the magnitude of the biomarker can be obtained using a decision tree approach for each image feature.

The initial custom biomarker is tested and provides performance measures, such as absolute and relative numbers of true positive objects (hits) and false positive objects, as well as the number of remaining suspicious mass lesion objects (misses) that are not yet found by the current development state of the custom biomarker. The initial output is investigated in a systematic manner. Image features that result in hits, false positives and misses are presented in a list and sorted by classification result. An interactive visual inspection of the list and the corresponding image objects helps the user, i.e., the person developing the custom biomarker, to identify new features and image segmentation procedures not yet used in the present state of the biomarker.

The visual inspection focuses on a subset of objects. If the number of false positives is much higher than the number of misses, then the visual inspection of the misses represents a less time consuming task. In that case, the reason for not detecting the suspicious masses might become obvious after a visual inspection of the misses. Compared to the hits that are already found, the appearance of the missed objects might be so much different that a new separate class description might be required. In this manner, a complex problem is divided into two or more less complex problems. So the extension of the class description of a suspicious mass is represented by several subclass descriptions. Through visual inspection of the misses, it becomes clear whether a new type of suspicious mass needs to be introduced. If this is the case, an additional biomarker for this new type of suspicious lesion is defined by taking the special features of this new object type into account. The revised custom biomarker is then tested, and the number of false positives is treated statistically with only minor visual inspection. The goal is to turn misses into hits without increasing the number of false positives.

A new subclass description can be created after a quick and sorted visual inspection of a small subgroup (in this case the misses). Thus, the software tool for optimizing the custom biomarker supports the visual inspection of subgroups of objects. Subgroups are defined within the list of objects and their image features. The software tool displays the corresponding objects as sections of the images containing the objects. The tool also displays the segmentation results. The segmentation results enable the user to judge whether the segmentation failed completely or was not precise enough. Depending on such a conclusion, either an additional segmentation can be introduced, or an existing segmentation procedure can be improved. In this way, the quality of the image features used by the custom biomarker is improved. New or modified segmentations allows for both improved as well as for new image features. This step-wise procedure involving visual inspection successively enhances the quality of the custom biomarker. Without visual inspection of the subgroups of objects, however, the process might not lead to a positive result.

Another way to enhance the quality of the custom biomarker is to recognize that a certain range of the values of an image feature result in false positives. This range of values can be excluded from contributing to the biomarker magnitude. The quality of the biomarker can also be enhanced by recognizing a correlation between certain hits and other available data in the database that can exclude false positives. For example, in the classification of one type of suspicious mass lesion, using the patient's age as a feature excludes some false positives. Using such meta data as features improves the custom biomarker by increasing the number of hits and decreasing the number of false positives.

The first implementation of a customer biomarker typically delivers many hits for a certain type of suspicious mass lesion but also too many false positives. Then using visual feedback and statistical investigation, image features for two types of suspicious mass lesion objects are developed. Additional biomarkers are developed using the visual feedback and statistical refinement for each different type of suspicious mass lesion in the training database.

When existing image features are not powerful enough adequately to differentiate visually recognized types of different suspicious mass lesions, new image features can be created, derived or improved upon. New image features can be calculated by combining existing features and metadata. For example, an image feature that measures breast density can be multiplied by the patient's age. New image features can also be derived from objects obtained by modifying or improving upon the initial segmentation used in the image analysis.

The custom biomarker for detecting suspicious mass lesions in mammograms is called the "Definiens Mammo" biomarker. The Definiens Mammo biomarker detects suspicious mass lesion objects for ten subclasses of lesion types. The Definiens Mammo biomarker was used to mark the mammograms from two hundred patients that were not present in the training database.

Many of the steps for defining image features and new types of segmentation are independent of the type of images being analyzed. Those standard step routines are included in the image analysis program. This is helpful because many of those routines might take weeks to accomplish with visual inspection, whereas it takes only minutes for the image analysis program to perform the routines on the images. The image analysis program automates the cycle from image analysis results, to data mining, back to image analysis, to data mining and back to image analysis, etc. In the case of the suspicious lesions described above, the misses are detected by the image analysis program in the first step. The misses are defined by the manually annotated objects for which no corresponding suspicious lesions were selected by the first iteration of the custom biomarker. The outlier objects are also detected. The desired result of the outlier detection must be defined by the user beforehand. For example, the user could require the best possible prediction of a clinical outcome derived from the image features. Or the user could require the best possible prediction of which drug is best suited to cure a specific disease detected by the image features in medical images. The outliers are defined as those results derived from the images that deviate most from the desired results, e.g., have the worst predictions compared to the actual clinical outcome. In other words, outliers are represented by those objects for which the results are worst compared to the desired results.

The software tool searches for additional image features by focusing on the outliers. As only a small sub-set of data needs to be investigated in more detail, many options can be tested. For instance, a large number of algorithmic combinations of existing image features are defined as new image features and their values are calculated for the outliers. Several different statistical investigations, such as cluster analysis, are then applied to the image features that mark the outliers. If clusters can indeed be found, a few non-outliers are picked randomly, and their new features are compared against those of the outliers. If the outliers and the non-outliers are marked differently by the new combined image features, the new image features are combined into a new version of the custom biomarker and tested with all of the existing data.

A similar procedure is applied to the modification of the segmentation procedures. A list of alternative segmentations and a list of segmentation extensions is tested on the outlier objects. The segmentation extensions and the alternative segmentations both lead to modified values of the old image features. The procedure for then selecting the correct new image features is similar to the procedure for selecting the correct combined new image features as described above. The difference is that the segmentations are usually much more time consuming than are the classifications.

The selection of new image features can also be knowledge driven. Normal ranges of the values of the image features are defined by the user beforehand. After a new segmentation is performed on outlier objects, the values of a large list of image features are compared to their predefined normal ranges. For example, the comparison can indicate a contrast of objects to their environment in certain image channels derived after the new segmentation. Based on what the user knows is normal and what is unusual, the image features for the outlier objects that are unusual are chosen as good candidates for further investigations taking more images and objects into account than just the outliers. The alternative segmentations that are first tested on the outlier objects can be selected by the user and picked from a library of algorithms.

Although the present invention has been described in connection with certain specific embodiments for instructional purposes, the present invention is not limited thereto. Accordingly, various modifications, adaptations, and combinations of various features of the described embodiments can be practiced without departing from the scope of the invention as set forth in the claims.

What is claimed is:

1. A method for displaying values of a table and images associated with one or more rows of the values on a graphical user interface, the method comprising:
   displaying the table in a first pane of the graphical user interface, wherein the table includes a user selectable row, wherein the user selectable row includes a reference value, a first numerical value and a second numerical value, wherein the reference value refers to a digital image of a slice of tissue, wherein the first numerical value is generated by performing image analysis on the digital image, and wherein the second numerical value indicates a health state of the slice of tissue; and
   displaying the digital image in a second pane of the graphical user interface in response to the user selecting the user selectable row.

2. The method of claim 1, wherein the digital image depicts only a portion the slice of tissue.

3. The method of claim 1, wherein the displayed image shows a classification of an object in the digital image.

4. The method of claim 1, wherein the first numerical value is taken from the group consisting of: an Allred score, a Gleason score, an Elston-Ellis score, and a HercepTest score.

5. The method of claim 1, wherein the health state of the slice of tissue is indicative of a disease free survival time.

6. The method of claim 1, wherein identified cells are indicated in the digital image displayed in the second pane, and wherein the identified cells are taken from the group consisting of: mitotic cells, tumor cells, stroma cells, cells exhibiting an overexpression of a protein, cells exhibiting an overamplification of a gene, and inflamed cells.

7. The method of claim 1, wherein an identified cell component is indicated in the digital image displayed in the second pane, and wherein the identified cell component is taken from the group consisting of: a nucleus, a cytoplasm and a membrane.

8. The method of claim 1, wherein an identified tissue region is indicated in the digital image displayed in the second pane, and wherein the identified tissue region is taken from the group consisting of: a tumor region, a stroma region, an inflamed region, an epithelial region and a glandular region.

9. The method of claim 1, wherein the user selectable row is marked with a color that corresponds to a classification of the digital image.

10. The method of claim 1, wherein the health state is determined by a statistical method using the first numerical value, and wherein the statistical method is taken from the group consisting of: applying a decision tree, applying a linear regression plot, applying a support vector machine, applying a Bayesian classifier.

11. The method of claim 1, further comprising:
    displaying a Kaplan Meier plot in a third pane of the graphical user interface, wherein a symbol is displayed in the Kaplan Meier plot in response to the user selecting the user selectable row, and wherein the symbol has a position in the Kaplan Meier plot defined by the health state.

12. The method of claim 1, further comprising:
    displaying a second digital image together with the digital image in an image gallery manner in the second pane in response to the user selecting a second user selectable row, wherein a second reference value in the second user selectable row refers to the second digital image.

13. The method of claim 12, wherein the second digital image displayed in the image gallery manner includes an outline of an object identified in the second digital image.

14. The method of claim 12, further comprising:
    ordering digital images displayed in the image gallery manner in the second pane to correspond to an order of user selectable rows in the table that correspond to the digital images.

15. The method of claim 14, wherein the ordering of the digital images occurs as the user selectable rows are selected.

16. The method of claim 14, wherein the ordered digital images depict portions of digital images of slices of tissue.

17. A computer program product tangibly embodied on a non-transitory computer-readable storage medium and comprising computer readable and executable program instructions that when executed by a processor provide a visual display of a user's graphical user interface on an interconnected display device, the graphical user interface comprising:
   a first pane displaying a graphical plot including a user selectable symbol, wherein the user selectable symbol is associated with a digital image of a slice of tissue, wherein the user selectable symbol has a position in the graphical plot defined by a first numerical value and a second numerical value, wherein a third numerical value is indicative of a health state of the slice of tissue, wherein the first and second numerical values are generated by image analysis of the digital image, and wherein the symbol represents the health state; and a second pane displaying images, wherein the second pane displays the digital image in response to the user selecting the selectable symbol.

18. The computer program product of claim 17, wherein the third numerical values is generated by image analysis of the digital image of the slice of tissue.

19. The computer program product of claim 17, wherein the first numerical value indicates an intensity of immunohistochemical staining of cancer cells in the digital image of the slice of tissue.

20. The computer program product of claim 17, wherein the second numerical value indicates a proportion of stained cells in a portion of the digital image.

21. The computer program product of claim 17, wherein the health state is a disease free survival time.

22. The computer program product of claim 17, wherein the third numerical value is indicative of the health state of a portion of the slice of tissue, and wherein the portion of the slice of tissue is taken from the group consisting of: normal tissue, in-situ cancer tissue, and distant metastasis tissue.

23. The computer program product of claim 17, wherein the health state of the slice of tissue is determined by image analysis by an expression status of a protein taken from the group consisting of: estrogen receptor protein (ER), progesterone receptor protein (PR), KI67 protein, and HER2neu protein.

24. The computer program product of claim 17, wherein the graphical plot is taken from the group consisting of: a scatter plot, a line plot, and a histogram plot.

25. A method comprising:
displaying a first image analysis value in a table in a first pane of a graphical user interface, wherein the first image analysis value is generated by analyzing a digital image of a slice of tissue using a first parameter;
displaying a list of selectable statistical methods in a second pane of the graphical user interface, wherein the list includes a statistical method;
computing a second parameter using the statistical method after the user has selected the statistical method; and
displaying a second image analysis value in the table after the user has selected the statistical method, wherein the second image analysis value is generated by analyzing the digital image using the second parameter.

26. The method of claim 25, further comprising:
displaying a new version of the digital image in a third pane of the graphical user interface after the user has selected the statistical method, wherein the new version of the digital image is generated by analyzing the digital image using the second parameter.

27. The method of claim 25, wherein the statistical method uses the first image analysis value to analyze the digital image.

28. The method of claim 25, wherein the first parameter is a decision threshold, and wherein the statistical method involves generating a decision tree.

29. The method of claim 25, wherein the first parameter is a segmentation threshold, and wherein the statistical method involves performing an aggregation method taken from the group consisting of: determining an average value, determining a standard deviation value, determining an absolute deviation value, and determining a quantile value.

30. The method of claim 25, wherein the statistical method is taken from the group consisting of: generating a decision tree, generating a linear regression plot, generating a support vector machine, generating a Bayes classifier.

31. The method of claim 25, wherein the slice of tissue includes tumor tissue.

32. The method of claim 25, wherein the first image analysis value is generated by analyzing only a portion of the digital image.

33. A method comprising:
displaying a table in a first pane of a graphical user interface, wherein the table includes a user selectable row, wherein the user selectable row includes a reference value, a first numerical value and a second numerical value, wherein the reference value refers to a digital image of a slice of tissue of a patient, wherein the first numerical value is generated by performing image analysis on the digital image, and wherein the second numerical value indicates a biological state; and
displaying the digital image in a second pane of the graphical user interface in response to a user selecting the user selectable row.

34. The method of claim 33, wherein the biological state corresponds to a health state of the patient.

35. The method of claim 33, wherein the biological state corresponds of to a health state of the slice of tissue.

36. The method of claim 33, wherein the health state of the slice of tissue is determined using gene expression information.

37. The method of claim 33, wherein the reference value includes a grouping of reference values.

38. The method of claim 33, wherein the displayed digital image includes an outline of an object in the digital image.

39. The method of claim 33, wherein the displayed digital image includes an outline in a common shape that encloses an object in the digital image, and wherein the common shape is taken from the group consisting of: a polygon, a circle and an oval.

* * * * *